(12) United States Patent
Amin et al.

(10) Patent No.: US 10,278,705 B2
(45) Date of Patent: *May 7, 2019

(54) HEART OCCLUSION DEVICES

(71) Applicant: W. L. Gore & Associates, Inc., Newark, DE (US)

(72) Inventors: Zahid Amin, Omaha, NE (US); Edward H. Cully, Flagstaff, AZ (US); Warren Cutright, Flagstaff, AZ (US); Coby C. Larsen, Flagstaff, AZ (US); Steven J. Masters, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 232 days.

This patent is subject to a terminal disclaimer.

(21) Appl. No.: 15/299,173

(22) Filed: Oct. 20, 2016

(65) Prior Publication Data

US 2017/0035435 A1 Feb. 9, 2017

Related U.S. Application Data

(60) Division of application No. 15/086,449, filed on Mar. 31, 2016, now Pat. No. 9,474,517, which is a
(Continued)

(51) Int. Cl.
*A61B 17/12* (2006.01)
*A61B 17/00* (2006.01)

(52) U.S. Cl.
CPC .... *A61B 17/12122* (2013.01); *A61B 17/0057* (2013.01); *A61B 17/12022* (2013.01);
(Continued)

(58) Field of Classification Search
CPC .......... A61B 17/0057; A61B 17/12122; A61B 17/12172; A61B 17/12145;
(Continued)

(56) References Cited

U.S. PATENT DOCUMENTS

| 283,653 A | 8/1883 | Paxson |
|---|---|---|
| 3,294,631 A | 12/1966 | Schrader et al. |

(Continued)

FOREIGN PATENT DOCUMENTS

| CN | 1218379 A | 6/1999 |
|---|---|---|
| CN | 1247460 A | 3/2000 |

(Continued)

OTHER PUBLICATIONS

International Search Report, International Application No. PCT/US97/17927, dated Feb. 10, 1998 (1 pg).
(Continued)

*Primary Examiner* — Phong Son H Dang

(57) ABSTRACT

This disclosure is directed to an aperture occlusion device and a method for occluding an aperture, including a perimembranous ventricular septal defect. The aperture occlusion device includes a wire frame element. The wire frame forms geometric shapes that include an occluder region and a securing region. The occluder region and the securing region are separated by an attachment region including a waist. The occluder region and securing region can include membranous coverings. The device can be attached to a delivery hub. The wires forming the occluder region and securing region can have a shape-memory capability such that they can be collapsed and distorted in a sheath during delivery, but resume and maintain their intended shape after delivery.

20 Claims, 27 Drawing Sheets

Related U.S. Application Data continuation of application No. 13/772,801, filed on Feb. 21, 2013, now abandoned, which is a continuation-in-part of application No. 13/210,198, filed on Aug. 15, 2011, now Pat. No. 9,138,213, which is a continuation-in-part of application No. 12/400,445, filed on Mar. 9, 2009, now Pat. No. 9,119,607.

(60) Provisional application No. 61/034,772, filed on Mar. 7, 2008.

(52) U.S. Cl.
CPC .. *A61B 17/12145* (2013.01); *A61B 17/12172* (2013.01); *A61B 2017/00243* (2013.01); *A61B 2017/00557* (2013.01); *A61B 2017/00575* (2013.01); *A61B 2017/00592* (2013.01); *A61B 2017/00597* (2013.01); *A61B 2017/00606* (2013.01); *A61B 2017/00615* (2013.01); *A61B 2017/00623* (2013.01); *A61B 2017/00632* (2013.01); *A61B 2017/00853* (2013.01); *A61B 2017/00867* (2013.01); *A61B 2017/12054* (2013.01); *A61B 2017/12095* (2013.01)

(58) Field of Classification Search
CPC .... A61B 17/12022; A61B 2017/12095; A61B 2017/00557; A61B 2017/00592; A61B 2017/00606; A61B 2017/00632; A61B 2017/00615; A61B 2017/12054; A61B 2017/00243; A61B 2017/00575; A61B 2017/00597; A61B 2017/00623; A61B 2017/00867; A61B 2017/00853
See application file for complete search history.

(56) References Cited

U.S. PATENT DOCUMENTS

| | | |
|---|---|---|
| 3,324,518 A | 6/1967 | Louderback |
| 3,447,533 A | 6/1969 | Spicer |
| 3,739,770 A | 6/1973 | Mori |
| 3,784,388 A | 1/1974 | King et al. |
| 3,824,631 A | 7/1974 | Burstein et al. |
| 3,874,388 A | 4/1975 | King et al. |
| 3,875,648 A | 4/1975 | Bone |
| 3,907,675 A | 9/1975 | Chapurlat et al. |
| 3,924,631 A | 12/1975 | Mancusi |
| 3,939,849 A | 2/1976 | Baxter et al. |
| 4,006,747 A | 2/1977 | Kronenthal et al. |
| 4,007,743 A | 2/1977 | Blake |
| 4,038,365 A | 7/1977 | Patil et al. |
| 4,113,912 A | 9/1978 | Okita |
| 4,149,327 A | 4/1979 | Hammer et al. |
| 4,193,138 A | 3/1980 | Okita |
| 4,425,908 A | 1/1984 | Simon |
| 4,525,374 A | 6/1985 | Vaillancourt |
| 4,610,674 A | 9/1986 | Suzuki et al. |
| 4,619,246 A | 10/1986 | Molgaard-Nielsen et al. |
| 4,626,245 A | 12/1986 | Weinstein |
| 4,693,249 A | 9/1987 | Schenck et al. |
| 4,696,300 A | 9/1987 | Anderson |
| 4,710,181 A | 12/1987 | Fuqua |
| 4,710,192 A | 12/1987 | Liotta et al. |
| 4,738,666 A | 4/1988 | Fuqua |
| 4,766,898 A | 8/1988 | Hardy et al. |
| 4,796,612 A | 1/1989 | Reese |
| 4,832,055 A | 5/1989 | Palestrant |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,917,793 A | 4/1990 | Pitt et al. |
| 4,921,479 A | 5/1990 | Grayzel |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,041,225 A | 8/1991 | Norman |
| 5,049,131 A | 9/1991 | Deuss |
| 5,049,275 A | 9/1991 | Gillberg-LaForce et al. |
| 5,078,736 A | 1/1992 | Behl |
| 5,090,422 A | 2/1992 | Dahl et al. |
| 5,098,440 A | 3/1992 | Hillstead |
| 5,106,913 A | 4/1992 | Yamaguchi et al. |
| 5,108,420 A | 4/1992 | Marks |
| 5,124,109 A | 6/1992 | Drossbach |
| 5,149,327 A | 9/1992 | Oshiyama |
| 5,152,144 A | 10/1992 | Andrie |
| 5,163,131 A | 11/1992 | Row et al. |
| 5,167,363 A | 12/1992 | Adkinson et al. |
| 5,167,637 A | 12/1992 | Okada et al. |
| 5,171,259 A | 12/1992 | Inoue |
| 5,176,659 A | 1/1993 | Mancini |
| 5,192,301 A | 3/1993 | Kamiya et al. |
| 5,222,974 A | 6/1993 | Kensey et al. |
| 5,226,879 A | 7/1993 | Ensminger et al. |
| 5,234,458 A | 8/1993 | Metais |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,269,809 A | 12/1993 | Hayhurst et al. |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,320,611 A | 6/1994 | Bonutti et al. |
| 5,334,217 A | 8/1994 | Das |
| 5,342,393 A | 8/1994 | Stack |
| 5,350,363 A | 9/1994 | Goode et al. |
| 5,350,399 A | 9/1994 | Erlebacher et al. |
| 5,354,308 A | 10/1994 | Simon et al. |
| 5,364,356 A | 11/1994 | Hofling |
| 5,397,331 A | 3/1995 | Himpens et al. |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,437,288 A | 8/1995 | Schwartz et al. |
| 5,443,727 A | 8/1995 | Gagnon |
| 5,443,972 A | 8/1995 | Kohama et al. |
| 5,451,235 A | 9/1995 | Lock et al. |
| 5,453,099 A | 9/1995 | Lee et al. |
| 5,478,353 A | 12/1995 | Yoon |
| 5,480,353 A | 1/1996 | Garza et al. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,549,959 A | 8/1996 | Compton |
| 5,562,632 A | 10/1996 | Davila et al. |
| 5,562,728 A | 10/1996 | Lazarus et al. |
| 5,571,169 A | 11/1996 | Plaia et al. |
| 5,575,816 A | 11/1996 | Rudnick et al. |
| 5,577,299 A | 11/1996 | Thompson et al. |
| 5,578,045 A | 11/1996 | Das |
| 5,591,206 A | 1/1997 | Moufarrege |
| 5,601,571 A | 2/1997 | Moss |
| 5,603,703 A | 2/1997 | Elsberry et al. |
| 5,618,311 A | 4/1997 | Gryskiewicz |
| 5,620,461 A | 4/1997 | Muijs Van de Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,662,701 A | 9/1997 | Plaia et al. |

(56) References Cited

U.S. PATENT DOCUMENTS

| | | |
|---|---|---|
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt |
| 5,709,707 A | 1/1998 | Lock et al. |
| 5,713,864 A | 2/1998 | Verkaart |
| 5,713,948 A | 2/1998 | Uflacker |
| 5,717,259 A | 2/1998 | Schexnayder |
| 5,720,754 A | 2/1998 | Middleman et al. |
| 5,725,552 A | 3/1998 | Kotula et al. |
| 5,725,553 A | 3/1998 | Moenning |
| 5,733,294 A | 3/1998 | Forber et al. |
| 5,733,337 A | 3/1998 | Carr et al. |
| 5,741,297 A | 4/1998 | Simon |
| 5,749,880 A | 5/1998 | Banas et al. |
| 5,755,762 A | 5/1998 | Bush |
| 5,769,882 A | 6/1998 | Fogarty et al. |
| 5,772,641 A | 6/1998 | Wilson |
| 5,776,162 A | 7/1998 | Kleshinski |
| 5,776,183 A | 7/1998 | Kanesaka et al. |
| 5,782,847 A | 7/1998 | Plaia et al. |
| 5,782,860 A | 7/1998 | Epstein et al. |
| 5,797,960 A | 8/1998 | Stevens et al. |
| 5,799,384 A | 9/1998 | Schwartz et al. |
| 5,800,436 A | 9/1998 | Lerch |
| 5,800,516 A | 9/1998 | Fine et al. |
| 5,810,884 A | 9/1998 | Kim |
| 5,820,594 A | 10/1998 | Fontirroche et al. |
| 5,823,956 A | 10/1998 | Roth et al. |
| 5,829,447 A | 11/1998 | Stevens et al. |
| 5,835,422 A | 11/1998 | Merritt |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,865,844 A | 2/1999 | Plaia et al. |
| 5,873,905 A | 2/1999 | Plaia et al. |
| 5,879,366 A | 3/1999 | Shaw et al. |
| 5,893,856 A | 4/1999 | Jacob et al. |
| 5,895,411 A | 4/1999 | Irie |
| 5,897,955 A | 4/1999 | Drumheller |
| 5,902,287 A | 5/1999 | Martin |
| 5,902,319 A | 5/1999 | Daley |
| 5,902,745 A | 5/1999 | Butler et al. |
| 5,904,703 A | 5/1999 | Gilson |
| 5,906,639 A | 5/1999 | Rudnick et al. |
| 5,919,200 A | 7/1999 | Stambaugh et al. |
| 5,924,424 A | 7/1999 | Stevens et al. |
| 5,925,060 A | 7/1999 | Forber |
| 5,928,250 A | 7/1999 | Koike et al. |
| 5,944,691 A | 8/1999 | Querns et al. |
| 5,944,738 A | 8/1999 | Amplatz et al. |
| 5,955,110 A | 9/1999 | Patel et al. |
| 5,957,490 A | 9/1999 | Sinnhuber |
| 5,957,953 A | 9/1999 | DiPoto et al. |
| 5,967,490 A | 10/1999 | Pike |
| 5,976,174 A | 11/1999 | Ruiz |
| 5,980,505 A | 11/1999 | Wilson |
| 5,989,268 A | 11/1999 | Pugsley et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,016,846 A | 1/2000 | Knittel et al. |
| 6,019,753 A | 2/2000 | Pagan |
| 6,024,756 A | 2/2000 | Huebsch et al. |
| 6,027,519 A | 2/2000 | Stanford |
| 6,030,007 A | 2/2000 | Bassily et al. |
| 6,051,007 A | 4/2000 | Hogendijk et al. |
| 6,053,939 A | 4/2000 | Okuda et al. |
| 6,056,760 A | 5/2000 | Koike et al. |
| 6,071,998 A | 6/2000 | Muller et al. |
| 6,074,401 A | 6/2000 | Gardiner et al. |
| 6,077,281 A | 6/2000 | Das |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,080,183 A | 6/2000 | Tsugita et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,123,715 A | 9/2000 | Amplatz |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,168,588 B1 | 1/2001 | Wilson |
| 6,171,329 B1 | 1/2001 | Shaw et al. |
| 6,174,322 B1 | 1/2001 | Schneidt |
| 6,174,330 B1 | 1/2001 | Stinson |
| 6,183,443 B1 | 2/2001 | Kratoska et al. |
| 6,183,496 B1 | 2/2001 | Urbanski |
| 6,187,039 B1 | 2/2001 | Hiles et al. |
| 6,190,353 B1 | 2/2001 | Makower et al. |
| 6,190,357 B1 | 2/2001 | Ferrari et al. |
| 6,197,016 B1 | 3/2001 | Fourkas et al. |
| 6,199,262 B1 | 3/2001 | Martin |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,258,091 B1 | 7/2001 | Sevrain et al. |
| 6,261,309 B1 | 7/2001 | Urbanski |
| 6,265,333 B1 | 7/2001 | Dzenis et al. |
| 6,270,500 B1 | 8/2001 | Lerch |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,290,689 B1 | 9/2001 | Delaney et al. |
| 6,290,721 B1 | 9/2001 | Heath |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,443 B1 | 11/2001 | Stone |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,427 B1 | 12/2001 | Watanabe et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,358,238 B1 | 3/2002 | Sherry |
| 6,364,853 B1 | 4/2002 | French et al. |
| 6,368,338 B1 | 4/2002 | Konya et al. |
| 6,371,904 B1 | 4/2002 | Sirimanne et al. |
| 6,375,625 B1 | 4/2002 | French et al. |
| 6,375,668 B1 | 4/2002 | Gifford et al. |
| 6,375,671 B1 | 4/2002 | Kobayashi et al. |
| 6,379,342 B1 | 4/2002 | Levinson |
| 6,379,363 B1 | 4/2002 | Herrington et al. |
| 6,379,368 B1 | 4/2002 | Corcoran et al. |

(56) References Cited

U.S. PATENT DOCUMENTS

| | | |
|---|---|---|
| 6,387,104 B1 | 5/2002 | Pugsley et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,443,972 B1 | 9/2002 | Bosma et al. |
| 6,450,987 B1 | 9/2002 | Kramer |
| 6,460,749 B1 | 10/2002 | Levinson et al. |
| 6,468,303 B1 | 10/2002 | Amplatz et al. |
| 6,478,773 B1 | 11/2002 | Gandhi et al. |
| 6,482,224 B1 | 11/2002 | Michler et al. |
| 6,488,706 B1 | 12/2002 | Solymar |
| 6,491,714 B1 | 12/2002 | Bennett |
| 6,494,846 B1 | 12/2002 | Margolis |
| 6,494,888 B1 | 12/2002 | Laufer et al. |
| 6,497,709 B1 | 12/2002 | Heath |
| 6,506,204 B2 | 1/2003 | Mazzocchi |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,554,849 B1 | 4/2003 | Jones et al. |
| 6,585,719 B2 | 7/2003 | Wang |
| 6,585,755 B2 | 7/2003 | Jackson et al. |
| 6,589,251 B2 | 7/2003 | Yee et al. |
| 6,596,013 B2 | 7/2003 | Yang et al. |
| 6,599,448 B1 | 7/2003 | Ehrhard et al. |
| 6,610,764 B1 | 8/2003 | Martin et al. |
| 6,623,506 B2 | 9/2003 | McGuckin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,652,556 B1 | 11/2003 | VanTassel et al. |
| 6,666,861 B1 | 12/2003 | Grabek |
| 6,669,707 B1 | 12/2003 | Swanstrom et al. |
| 6,669,713 B2 | 12/2003 | Adams |
| 6,669,722 B2 | 12/2003 | Chen et al. |
| 6,685,707 B2 | 2/2004 | Roman et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,755,834 B2 | 6/2004 | Amis |
| 6,786,915 B2 | 9/2004 | Akerfeldt et al. |
| 6,828,357 B1 | 12/2004 | Martin et al. |
| 6,838,493 B2 | 1/2005 | Williams et al. |
| 6,855,126 B2 | 2/2005 | Flinchbaugh |
| 6,860,895 B1 | 3/2005 | Akerfeldt et al. |
| 6,866,669 B2 | 3/2005 | Buzzard et al. |
| 6,867,247 B2 | 3/2005 | Williams et al. |
| 6,867,248 B1 | 3/2005 | Martin et al. |
| 6,867,249 B2 | 3/2005 | Lee |
| 6,921,401 B2 | 7/2005 | Lerch et al. |
| 6,921,410 B2 | 7/2005 | Porter |
| 6,939,352 B2 | 9/2005 | Buzzard et al. |
| 6,994,092 B2 | 2/2006 | van der Burg et al. |
| 7,044,134 B2 | 5/2006 | Khairkhahan et al. |
| 7,048,738 B1 | 5/2006 | Wellisz et al. |
| 7,097,653 B2 | 8/2006 | Freudenthal et al. |
| 7,128,073 B1 | 10/2006 | van der Burg et al. |
| 7,149,587 B2 | 12/2006 | Wardle et al. |
| 7,152,605 B2 | 12/2006 | Khairkhahan et al. |
| 7,165,552 B2 | 1/2007 | Deem et al. |
| 7,198,631 B2 | 4/2007 | Kanner et al. |
| 7,207,402 B2 | 4/2007 | Björk |
| 7,223,271 B2 | 5/2007 | Muramatsu et al. |
| 7,238,188 B2 | 7/2007 | Nesper et al. |
| 7,335,426 B2 | 2/2008 | Marton et al. |
| 7,361,178 B2 | 4/2008 | Hearn et al. |
| 7,381,216 B2 | 6/2008 | Buzzard et al. |
| 7,431,729 B2 | 10/2008 | Chanduszko |
| 7,452,363 B2 | 11/2008 | Ortiz |
| 7,481,832 B1 | 1/2009 | Meridew et al. |
| 7,582,104 B2 | 9/2009 | Corcoran et al. |
| 7,597,704 B2 | 10/2009 | Frazier et al. |
| 7,658,748 B2 | 2/2010 | Marino et al. |
| 7,678,123 B2 | 3/2010 | Chanduszko |
| 7,704,268 B2 | 4/2010 | Chanduszko |
| 7,735,493 B2 | 6/2010 | van der Burg et al. |
| 7,780,700 B2 | 8/2010 | Frazier et al. |
| 7,842,053 B2 | 11/2010 | Chanduszko et al. |
| 7,871,419 B2 | 1/2011 | Devellian et al. |
| 7,875,052 B2 | 1/2011 | Kawaura et al. |
| 7,887,562 B2 | 2/2011 | Young et al. |
| 7,905,901 B2 | 3/2011 | Corcoran et al. |
| 7,918,872 B2 | 4/2011 | Mitelberg et al. |
| 8,034,061 B2 | 10/2011 | Amplatz et al. |
| 8,062,325 B2 | 11/2011 | Mitelberg et al. |
| 8,118,833 B2 | 2/2012 | Seibold et al. |
| 8,257,389 B2 | 9/2012 | Chanduszko et al. |
| 8,277,480 B2 | 10/2012 | Callaghan et al. |
| 8,308,760 B2 | 11/2012 | Chanduszko |
| 8,361,110 B2 | 1/2013 | Chanduszko |
| 8,480,706 B2 | 7/2013 | Chanduszko et al. |
| 8,551,135 B2 | 10/2013 | Kladakis et al. |
| 8,753,362 B2 | 6/2014 | Widomski et al. |
| 8,764,790 B2 | 7/2014 | Thommen et al. |
| 8,764,848 B2 | 7/2014 | Callaghan et al. |
| 8,821,528 B2 | 9/2014 | McGuckin et al. |
| 8,858,576 B2 | 10/2014 | Takahashi et al. |
| 9,005,242 B2 | 4/2015 | Cahill |
| 9,119,607 B2 | 9/2015 | Amin |
| 9,138,213 B2 | 9/2015 | Amin et al. |
| 9,326,759 B2 | 5/2016 | Chanduszko et al. |
| 9,474,517 B2 | 10/2016 | Amin et al. |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2001/0049551 A1 | 12/2001 | Tseng et al. |
| 2002/0010481 A1 | 1/2002 | Jayaraman |
| 2002/0019648 A1 | 2/2002 | Akerfeldt et al. |
| 2002/0022859 A1 | 2/2002 | Hogendijk |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058980 A1 | 5/2002 | Sass |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0095183 A1 | 7/2002 | Casset et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0099437 A1 | 7/2002 | Anson et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0143292 A1 | 10/2002 | Flinchbaugh |
| 2002/0156475 A1 | 10/2002 | Lerch et al. |

(56) References Cited

U.S. PATENT DOCUMENTS

| | | |
|---|---|---|
| 2002/0156499 A1 | 10/2002 | Konya et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Borillo et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0113868 A1 | 6/2003 | Flor et al. |
| 2003/0120337 A1 | 6/2003 | Van Tassel et al. |
| 2003/0130683 A1 | 7/2003 | Andreas et al. |
| 2003/0139819 A1 | 7/2003 | Beer et al. |
| 2003/0150821 A1 | 8/2003 | Bates et al. |
| 2003/0153901 A1 | 8/2003 | Herweck et al. |
| 2003/0171774 A1 | 9/2003 | Freudenthal et al. |
| 2003/0187390 A1 | 10/2003 | Bates et al. |
| 2003/0191495 A1 | 10/2003 | Ryan et al. |
| 2003/0195530 A1 | 10/2003 | Thill |
| 2003/0195555 A1 | 10/2003 | Khairkhahan et al. |
| 2003/0204203 A1 | 10/2003 | Khairkhahan et al. |
| 2003/0225421 A1 | 12/2003 | Peavey et al. |
| 2003/0225439 A1 | 12/2003 | Cook et al. |
| 2004/0006330 A1 | 1/2004 | Fangrow |
| 2004/0044361 A1 | 3/2004 | Frazier et al. |
| 2004/0044364 A1 | 3/2004 | DeVries et al. |
| 2004/0073242 A1 | 4/2004 | Chanduszko |
| 2004/0098042 A1 | 5/2004 | Devellian et al. |
| 2004/0116959 A1 | 6/2004 | McGuckin et al. |
| 2004/0127919 A1 | 7/2004 | Trout et al. |
| 2004/0133230 A1 | 7/2004 | Carpenter et al. |
| 2004/0133236 A1 | 7/2004 | Chanduszko |
| 2004/0143294 A1 | 7/2004 | Corcoran et al. |
| 2004/0167566 A1 | 8/2004 | Beulke et al. |
| 2004/0176799 A1 | 9/2004 | Chanduszko et al. |
| 2004/0186510 A1 | 9/2004 | Weaver |
| 2004/0210301 A1 | 10/2004 | Obermiller |
| 2004/0220596 A1 | 11/2004 | Frazier et al. |
| 2004/0220610 A1 | 11/2004 | Kreidler et al. |
| 2004/0230222 A1 | 11/2004 | van der Burg et al. |
| 2004/0234567 A1 | 11/2004 | Dawson |
| 2004/0254594 A1 | 12/2004 | Alfaro |
| 2005/0025809 A1 | 2/2005 | Hasirci et al. |
| 2005/0038470 A1 | 2/2005 | van der Burg et al. |
| 2005/0043759 A1 | 2/2005 | Chanduszko |
| 2005/0055039 A1 | 3/2005 | Burnett et al. |
| 2005/0065548 A1 | 3/2005 | Marino et al. |
| 2005/0067523 A1 | 3/2005 | Zach et al. |
| 2005/0070935 A1 | 3/2005 | Ortiz |
| 2005/0080476 A1 | 4/2005 | Gunderson et al. |
| 2005/0113868 A1 | 5/2005 | Devellian et al. |
| 2005/0119690 A1 | 6/2005 | Mazzocchi et al. |
| 2005/0182426 A1 | 8/2005 | Adams et al. |
| 2005/0187564 A1 | 8/2005 | Jayaraman |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0267523 A1 | 12/2005 | Devellian et al. |
| 2005/0267525 A1 | 12/2005 | Chanduszko |
| 2005/0267572 A1 | 12/2005 | Schoon et al. |
| 2005/0273135 A1 | 12/2005 | Chanduszko et al. |
| 2005/0288706 A1 | 12/2005 | Widomski et al. |
| 2005/0288786 A1 | 12/2005 | Chanduszko |
| 2006/0020332 A1 | 1/2006 | Lashinski et al. |
| 2006/0025790 A1 | 2/2006 | de Winter et al. |
| 2006/0030884 A1 | 2/2006 | Yeung et al. |
| 2006/0052821 A1 | 3/2006 | Abbott et al. |
| 2006/0106447 A1 | 5/2006 | Opolski |
| 2006/0109073 A1 | 5/2006 | Allison et al. |
| 2006/0116710 A1 | 6/2006 | Corcoran et al. |
| 2006/0122646 A1 | 6/2006 | Corcoran et al. |
| 2006/0122647 A1 | 6/2006 | Callaghan et al. |
| 2006/0167494 A1 | 7/2006 | Suddaby |
| 2006/0206148 A1 | 9/2006 | Khairkhahan et al. |
| 2006/0217764 A1 | 9/2006 | Abbott et al. |
| 2006/0224183 A1 | 10/2006 | Freudenthal |
| 2006/0235463 A1 | 10/2006 | Freudenthal et al. |
| 2006/0241690 A1 | 10/2006 | Amplatz et al. |
| 2006/0265004 A1 | 11/2006 | Callaghan et al. |
| 2006/0271089 A1 | 11/2006 | Alejandro et al. |
| 2006/0276839 A1 | 12/2006 | McGuckin |
| 2007/0010851 A1 | 1/2007 | Chanduszko et al. |
| 2007/0066994 A1 | 3/2007 | Blaeser et al. |
| 2007/0096048 A1 | 5/2007 | Clerc |
| 2007/0112381 A1 | 5/2007 | Figulla et al. |
| 2007/0118176 A1 | 5/2007 | Opolski et al. |
| 2007/0129755 A1 | 6/2007 | Abbott et al. |
| 2007/0167981 A1 | 7/2007 | Opolski et al. |
| 2007/0179474 A1 | 8/2007 | Cahill et al. |
| 2007/0185529 A1 | 8/2007 | Coleman et al. |
| 2007/0191884 A1 | 8/2007 | Eskridge et al. |
| 2007/0225760 A1 | 9/2007 | Moszner et al. |
| 2007/0233186 A1 | 10/2007 | Meng |
| 2007/0244517 A1 | 10/2007 | Callaghan |
| 2007/0244518 A1 | 10/2007 | Callaghan |
| 2007/0250081 A1 | 10/2007 | Cahill et al. |
| 2007/0250115 A1 | 10/2007 | Opolski et al. |
| 2007/0265656 A1 | 11/2007 | Amplatz et al. |
| 2007/0276415 A1 | 11/2007 | Kladakis et al. |
| 2007/0282430 A1 | 12/2007 | Thommen et al. |
| 2008/0015633 A1 | 1/2008 | Abbott et al. |
| 2008/0058800 A1 | 3/2008 | Collins et al. |
| 2008/0065149 A1 | 3/2008 | Thielen et al. |
| 2008/0077180 A1 | 3/2008 | Kladakis et al. |
| 2008/0086168 A1 | 4/2008 | Cahill |
| 2008/0091234 A1 | 4/2008 | Kladakis |
| 2008/0109073 A1 | 5/2008 | Lashinski et al. |
| 2008/0119886 A1 | 5/2008 | Greenhalgh et al. |
| 2008/0119891 A1 | 5/2008 | Miles et al. |
| 2008/0147111 A1 | 6/2008 | Johnson et al. |
| 2008/0208214 A1 | 8/2008 | Sato et al. |
| 2008/0228218 A1 | 9/2008 | Chanduszko |
| 2008/0249562 A1 | 10/2008 | Cahill |
| 2008/0262518 A1 | 10/2008 | Freudenthal |
| 2008/0312666 A1 | 12/2008 | Ellingwood et al. |
| 2009/0012559 A1 | 1/2009 | Chanduszko |
| 2009/0054912 A1 | 2/2009 | Heanue et al. |
| 2009/0062841 A1 | 3/2009 | Amplatz et al. |
| 2009/0062844 A1 | 3/2009 | Tekulve et al. |
| 2009/0069885 A1 | 3/2009 | Rahdert et al. |
| 2009/0076541 A1 | 3/2009 | Chin et al. |
| 2009/0088795 A1 | 4/2009 | Cahill |
| 2009/0118745 A1 | 5/2009 | Paul et al. |
| 2009/0204133 A1 | 8/2009 | Melzer et al. |
| 2009/0228038 A1 | 9/2009 | Amin |
| 2009/0292310 A1 | 11/2009 | Chin et al. |
| 2009/0306706 A1 | 12/2009 | Osypka |
| 2010/0004679 A1 | 1/2010 | Osypka |
| 2010/0121370 A1 | 5/2010 | Kariniemi |
| 2010/0145382 A1 | 6/2010 | Chanduszko |
| 2010/0160944 A1 | 6/2010 | Teoh et al. |
| 2010/0211046 A1 | 8/2010 | Adams et al. |
| 2010/0234878 A1 | 9/2010 | Hruska et al. |
| 2010/0234884 A1 | 9/2010 | Lafontaine et al. |
| 2010/0234885 A1 | 9/2010 | Frazier et al. |
| 2010/0324538 A1 | 12/2010 | Van Orden |
| 2010/0324585 A1 | 12/2010 | Miles et al. |
| 2010/0324652 A1 | 12/2010 | Aurilia et al. |
| 2011/0040324 A1 | 2/2011 | McCarthy et al. |
| 2011/0054519 A1 | 3/2011 | Neuss |
| 2011/0087146 A1 | 4/2011 | Ryan et al. |
| 2011/0184439 A1 | 7/2011 | Anderson et al. |
| 2011/0184456 A1 | 7/2011 | Grandfield et al. |
| 2011/0218479 A1 | 9/2011 | Rottenberg et al. |
| 2011/0295298 A1 | 12/2011 | Moszner |
| 2011/0301630 A1 | 12/2011 | Hendriksen et al. |

(56) References Cited

U.S. PATENT DOCUMENTS

| | | |
|---|---|---|
| 2012/0029556 A1 | 2/2012 | Masters |
| 2012/0071918 A1 | 3/2012 | Amin et al. |
| 2012/0116528 A1 | 5/2012 | Nguyen |
| 2012/0143242 A1 | 6/2012 | Masters |
| 2012/0150218 A1 | 6/2012 | Sandgren et al. |
| 2012/0197292 A1 | 8/2012 | Chin-Chen et al. |
| 2012/0245623 A1 | 9/2012 | Kariniemi et al. |
| 2012/0316597 A1 | 12/2012 | Fitz et al. |
| 2013/0041404 A1 | 2/2013 | Amin et al. |
| 2013/0218202 A1 | 8/2013 | Masters |
| 2013/0231684 A1 | 9/2013 | Aurilia et al. |
| 2013/0245666 A1 | 9/2013 | Larsen et al. |
| 2013/0282054 A1 | 10/2013 | Osypka |
| 2013/0296925 A1 | 11/2013 | Chanduszko et al. |
| 2014/0039543 A1 | 2/2014 | Willems et al. |
| 2014/0142610 A1 | 5/2014 | Larsen et al. |
| 2014/0194921 A1 | 7/2014 | Akpinar |
| 2014/0207185 A1 | 7/2014 | Goble et al. |
| 2014/0309684 A1 | 10/2014 | Al-Qbandi et al. |
| 2014/0343602 A1 | 11/2014 | Cox et al. |
| 2015/0005809 A1 | 1/2015 | Ayres et al. |
| 2015/0039023 A1 | 2/2015 | De Canniere et al. |
| 2015/0066077 A1 | 3/2015 | Akpinar |
| 2015/0148731 A1 | 5/2015 | McNamara et al. |
| 2015/0196288 A1 | 7/2015 | Van Orden |
| 2017/0156843 A1 | 6/2017 | Clerc |

FOREIGN PATENT DOCUMENTS

| | | |
|---|---|---|
| CN | 101460102 A | 6/2009 |
| DE | 9413645 U1 | 10/1994 |
| DE | 9413649 U1 | 10/1994 |
| DE | 102006036649 A1 | 10/2007 |
| EP | 0362113 A1 | 4/1990 |
| EP | 0474887 A1 | 3/1992 |
| EP | 0839549 A1 | 5/1998 |
| EP | 0861632 A1 | 9/1998 |
| EP | 1013227 A2 | 6/2000 |
| EP | 1046375 A1 | 10/2000 |
| EP | 1222897 A2 | 7/2002 |
| EP | 2240125 B1 | 10/2010 |
| EP | 2340770 A1 | 7/2011 |
| EP | 2524653 A1 | 11/2012 |
| JP | H0613686 Y2 | 4/1994 |
| JP | H10244611 A | 9/1998 |
| JP | 2000505668 A | 5/2000 |
| JP | 2000300571 A | 10/2000 |
| JP | 2002513308 A | 5/2002 |
| JP | 2004512153 A | 4/2004 |
| JP | 2004534390 A | 11/2004 |
| JP | 2005521447 A | 7/2005 |
| JP | 2005521818 A | 7/2005 |
| JP | 2005261597 A | 9/2005 |
| JP | 2006230800 A | 9/2006 |
| JP | 2007526087 A1 | 9/2007 |
| JP | 2007535986 A | 12/2007 |
| JP | 2009000497 A | 1/2009 |
| JP | 2009512521 A | 3/2009 |
| JP | 2009514624 A | 4/2009 |
| JP | 2009160402 A | 7/2009 |
| JP | 2010525896 A | 7/2010 |
| JP | 2012519572 A | 8/2012 |
| KR | 20010040637 A | 5/2001 |
| RU | 2208400 C2 | 7/2003 |
| RU | 84711 U1 | 7/2009 |
| SU | 1377052 A1 | 2/1988 |
| WO | WO9319803 A1 | 10/1993 |
| WO | WO9601591 A1 | 1/1996 |
| WO | WO9625179 A1 | 8/1996 |
| WO | WO9631157 A1 | 10/1996 |
| WO | WO9640305 A1 | 12/1996 |
| WO | WO9807375 A1 | 2/1998 |
| WO | WO9808462 A2 | 3/1998 |
| WO | WO9816174 A1 | 4/1998 |
| WO | WO9818864 A1 | 5/1998 |
| WO | WO9829026 A2 | 7/1998 |
| WO | WO9851812 A2 | 11/1998 |
| WO | WO9905977 A1 | 2/1999 |
| WO | WO9918862 A1 | 4/1999 |
| WO | WO9918864 A1 | 4/1999 |
| WO | WO9918870 A1 | 4/1999 |
| WO | WO9918871 A1 | 4/1999 |
| WO | WO9930640 A1 | 6/1999 |
| WO | WO9939646 A1 | 8/1999 |
| WO | WO9966846 A1 | 12/1999 |
| WO | 2000012012 A1 | 3/2000 |
| WO | WO0027292 A1 | 5/2000 |
| WO | WO0044428 A2 | 8/2000 |
| WO | WO0051500 A1 | 9/2000 |
| WO | WO0108600 A2 | 2/2001 |
| WO | 2001017435 A1 | 3/2001 |
| WO | WO0119256 A1 | 3/2001 |
| WO | WO0121247 A1 | 3/2001 |
| WO | WO0128432 A1 | 4/2001 |
| WO | WO0130268 A1 | 5/2001 |
| WO | WO2001049185 A1 | 7/2001 |
| WO | WO0178596 A1 | 10/2001 |
| WO | WO2001072367 A1 | 10/2001 |
| WO | WO0193783 A2 | 12/2001 |
| WO | WO0217809 A1 | 3/2002 |
| WO | WO0224106 A2 | 3/2002 |
| WO | WO0238051 A2 | 5/2002 |
| WO | WO03001893 A2 | 1/2003 |
| WO | 03024337 A1 | 3/2003 |
| WO | WO0305152 A2 | 7/2003 |
| WO | WO03053493 A2 | 7/2003 |
| WO | WO03061481 A1 | 7/2003 |
| WO | WO03063732 A2 | 8/2003 |
| WO | WO03077733 A2 | 9/2003 |
| WO | WO03082076 A2 | 10/2003 |
| WO | 2003103476 A2 | 12/2003 |
| WO | WO03103476 A2 | 12/2003 |
| WO | WO2004012603 A2 | 2/2004 |
| WO | 2004032993 A2 | 4/2004 |
| WO | 2004037333 A1 | 5/2004 |
| WO | 2004043266 A2 | 5/2004 |
| WO | 2004043508 A1 | 5/2004 |
| WO | 2004047649 A1 | 6/2004 |
| WO | 2004052213 A1 | 6/2004 |
| WO | 2004067092 A2 | 8/2004 |
| WO | 2004101019 A2 | 11/2004 |
| WO | 2005006990 A2 | 1/2005 |
| WO | 2005018728 A2 | 3/2005 |
| WO | 2005027752 A1 | 3/2005 |
| WO | 2005032335 A2 | 4/2005 |
| WO | 2005034724 A2 | 4/2005 |
| WO | 2005074813 A1 | 8/2005 |
| WO | 2005092203 A2 | 10/2005 |
| WO | 2005110240 A1 | 11/2005 |
| WO | 2005112779 A1 | 12/2005 |
| WO | 2006036837 A2 | 4/2006 |
| WO | 2006041612 A2 | 4/2006 |
| WO | 2006062711 A2 | 6/2006 |
| WO | 2006102213 A1 | 9/2006 |
| WO | 2007124862 A2 | 11/2007 |
| WO | 2007140797 A1 | 12/2007 |
| WO | 2008002983 A1 | 1/2008 |
| WO | 2008125689 A1 | 10/2008 |
| WO | 2008137603 A1 | 11/2008 |
| WO | 2008153872 A2 | 12/2008 |
| WO | 2008156464 A1 | 12/2008 |
| WO | 2011044486 A1 | 4/2011 |
| WO | 2011153548 A1 | 12/2011 |
| WO | 2012003317 A1 | 1/2012 |

OTHER PUBLICATIONS

Isotalo, T. et al., "Biocompatibility Testing of a New Bioabsorbable X-Ray Positive SR-PLA 96/4 Urethral Stent", The Journal of Urology. vol. 162, pp. 1764-1767, Nov. 1999.

Jackson et al., "55-nitinol-the alloy with a memory—its physical metallurgy, properties and applications," NASA, pp. 24-25, 1972.

(56) References Cited

OTHER PUBLICATIONS

Kimura, A., et al., "Effects of Neutron Irradiation on the Transformation Behavior in Ti—Ni Alloys," Abstract, Proceedings of the Int'l Conf. on Mariensitic Transformations, 1992, pp. 935-940.
Klima, U., et al., "Magnetic Vascular Port in Minimally Invasive Direct Coronary Artery Bypass Grafting," Circulation, 2004, pp. 11-55-11-60.
Meier and Lock, "Contemporary management of patent foramen ovale," Circulation., Jan. 7, 2003; 107(1):5-9.
Parviainen, M. et al., "A New Biodegradable Stent for the Pancreaticojejunal Anastomosis After Pancreaticoduodenal Resection: In Vitro Examination and Pilot Experiences in Humans", Pancreas, vol. 21, No. 1, pp. 14-21, 2000.
Ramanathan, G., et. al., "Experimental and Computational Methods for Shape Memory Alloys," 15th ASCE Engineering Mechanics Conference, Jun. 2-5, 2002, 12 pages.
Ruddy, A. C. et al., "Rheological, Mechanical and Thermal Behaviour of Radipaque Filled Polymers", Polymer Processing Research Centre, School of Chemical Engineering, Queen's University of Belfast, pp. 167-171, 2005.
Ruiz, et al., "The puncture technique: A new method for transcatheter closure of patent foramen ovale," Catheterization and Cardiovascular Interventions, 2001, vol. 53, pp. 369-372.
Schaffer and Gordon, "Engineering Characteristics of Drawn Filled Nitinol Tube" SMST-2003: Proceedings of the International Conference on Shape Memory and Superelastic Technologies (ASM International), pp. 109-118, 2004.
Shabalovskaya, "Surface, corrosion and biocompatibility aspects of Nitinol as an implant material," Biomed Mater Eng., 2002;12(1):69-109.
Stein, H., "Telemanipulator-gestutzte Applikation eines magnetischen Gefass-Kopplers am schlagenden Herzen mit dem da Vinci'—Surgical-System," Biomedizinische Technik, 2003, vol. 48 (9), pp. 230-234.
Stockel, "Nitinol Medical Devices and Implants," Min Invas Ther & Allied Technol 9(2), Cordis Corporation—Nitinol/Devices and Components, Fremont, CA, USA, 2000pp. 81-88.
Uchil, "Shape Memory Alloys—Characterization Techniques," Pramana—Journal of Physics, 2002 vol. 58 (5)(6), pp. 1131-1139.
Vaajanen et al., "Expansion and fixation properties of a new braided biodegradable urethral stent: an experimental study in the rabbit," The Journal of Urology, J Urol., Mar. 2003; 169(3):1171-1174.
European Search Report issued in 16193808.9, dated May 19, 2017, 9 pages.
Athanasiou, "Coronary artery bypass with the use of a magnetic distal anastomotic device: surgical technique and preliminary experience," Heart Surg Forum., 2004;7(6):4 pages.
Bachthaler, M. et al., "Corrosion of Tungsten Coils After Peripheral Vascular Embolization Theraphy: Influence on Outcome and Tungsten Load", Catherization and Cardiovascular Interventions, vol. 62, pp. 380-384, 2004.
Chinese Search Report in Application No. 200980158768.9, dated Jun. 16, 2013, 4 pages.
European Examination Report, European Application No. 03729663.9, dated Jul. 16, 2008 (5 Pages).
European Examination Report, European Application No. 03731562.9, dated Jul. 18, 2008 (3 Pages).
European Examination Report, European Application No. 03779297.5, dated Mar. 15, 2007 (6 Pages).
European Examination Report, European Application No. 04781644.2, dated Aug. 23, 2007 (4 Pages).
European Search Report, European Application No. 03729663.9, dated Feb. 20, 2008 (3 Pages).
European Search Report, European Application No. 11007412.7, dated Jan. 19, 2012, 5 pages.
European Search Report, European Application No. 12150504.4, dated Jul. 2, 2012, 5 pages.
Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.
Filsoufi, F., et al., "Automated Distal Coronary Bypass with a Novel Magnetic Coupler (MVP system)," J. Thoracic and Cardiovascular Surgery, vol. 127(1 ), pp. 185-192.
International Preliminary Report on Patentability and Written Opinion for PCT/US2009/004307, dated Sep. 13, 2011, 8 pages.
International Preliminary Report on Patentability and Written Opinion for PCT/US2010/039354 dated Jan. 4, 2012, 5 pages.
International Preliminary Report on Patentability and Written Opinion for PCT/US2010/039358 dated Jan. 4, 2012, 7 pages.
International Preliminary Report on Patentability for PCT/US2012/063598, dated May 13, 2014, 7 pages.
International Preliminary Report on Patentability issued in PCT/US2015/034452, dated Dec. 15, 2016, 10 pages.
International Search Report and Written Opinion for PCT/US2012/063598, dated Feb. 4, 2013, 11 pages.
International Search Report and Written Opinion for PCT/US2014/011980, dated Sep. 9, 2014, 31 pages.
International Search Report and Written Opinion for PCT/US2014/017129 dated May 14, 2014, 8 pages.
International Search Report and Written Opinion, International Patent Application No. PCT/US06/41255, dated Jun. 13, 2008 (4 pgs).
International Search Report and Written Opinion, International Patent Application No. PCT/US08/59429, dated Sep. 5, 2008 (7 pgs).
International Search Report and Written Opinion; dated Feb. 22, 2013; World Intellectual Property Organization (WIPO) (International Bureau of); PCT/US2012/050358; 14 pages.
International Search Report for International Patent Application No. PCT/AU03/00759, dated Aug. 25, 2003, 4 pages.
International Search Report for PCT/US2009/004307, dated Nov. 27, 2009, 6 pages.
International Search Report for PCT/US2010/039354, dated Sep. 15, 2010, 5 pages.
International Search Report for PCT/US2010/039358 dated Sep. 3, 2010, 5 pages.
International Search Report for PCT/US2012/050785, dated Nov. 23, 2012, 6 pages.
International Search Report, International Application No. PCT/US02/40850 dated Jun. 19, 2003 (4 pgs).
International Search Report, International Application No. PCT/US03/01050, dated Jul. 8, 2003 (1 pg).
International Search Report, International Application No. PCT/US03/09051, dated Sep. 29, 2003 (2 pgs).
International Search Report, International Application No. PCT/US03/17390, dated Oct. 6, 2003 (2 pgs).
International Search Report, International Application No. PCT/US03/17715, dated Mar. 24, 2004 (2 pages).
International Search Report, International Application No. PCT/US03/32133, dated Apr. 22, 2004 (1 pg).
International Search Report, International Application No. PCT/US03/34003 dated Mar. 10, 2004 (4 pgs).
International Search Report, International Application No. PCT/US03/35479, dated Apr. 14, 2004 (3 pgs).
International Search Report, International Application No. PCT/US03/35998 dated Jun. 16, 2004 (5 pgs).
International Search Report, International Application No. PCT/US03/39253, dated Apr. 19, 2004 (4 pgs).
International Search Report, International Application No. PCT/US04/022643, dated Mar. 31, 2005 (5 pgs).
International Search Report, International Application No. PCT/US04/026998, dated Apr. 22, 2005 (5 pgs).
International Search Report, International Application No. PCT/US04/029978, dated Jan. 26, 2005 (3 pgs).
International Search Report, International Application No. PCT/US05/006703, dated Jul. 25, 2005 (3 pgs).
International Search Report, International Application No. PCT/US05/013705 dated Aug. 4, 2005 (4 pgs).
International Search Report, International Application No. PCT/US05/015382, dated Oct. 6, 2005 (4 pgs).
International Search Report, International Application No. PCT/US05/34276, dated Oct. 4, 2007, 1 page.

(56) References Cited

OTHER PUBLICATIONS

International Search Report, International Application No. PCT/US06/009978, dated Jul. 13, 2006 (2 pgs).
International Search Report, International Application No. PCT/US07/065546, dated Oct. 29, 2007. 2 pages.
International Search Report, International Application No. PCT/US2007/065526, dated Aug. 8, 2007 (4 pgs).
International Search Report, International Application No. PCT/US2007/065541, dated Aug. 7, 2007 (3 pgs).
International Search Report, International Application No. PCT/US97/14822, dated Feb. 20, 1998 (2 pgs).
European Search Report from EP17192489.7, dated Nov. 30, 2017, 6 pages.

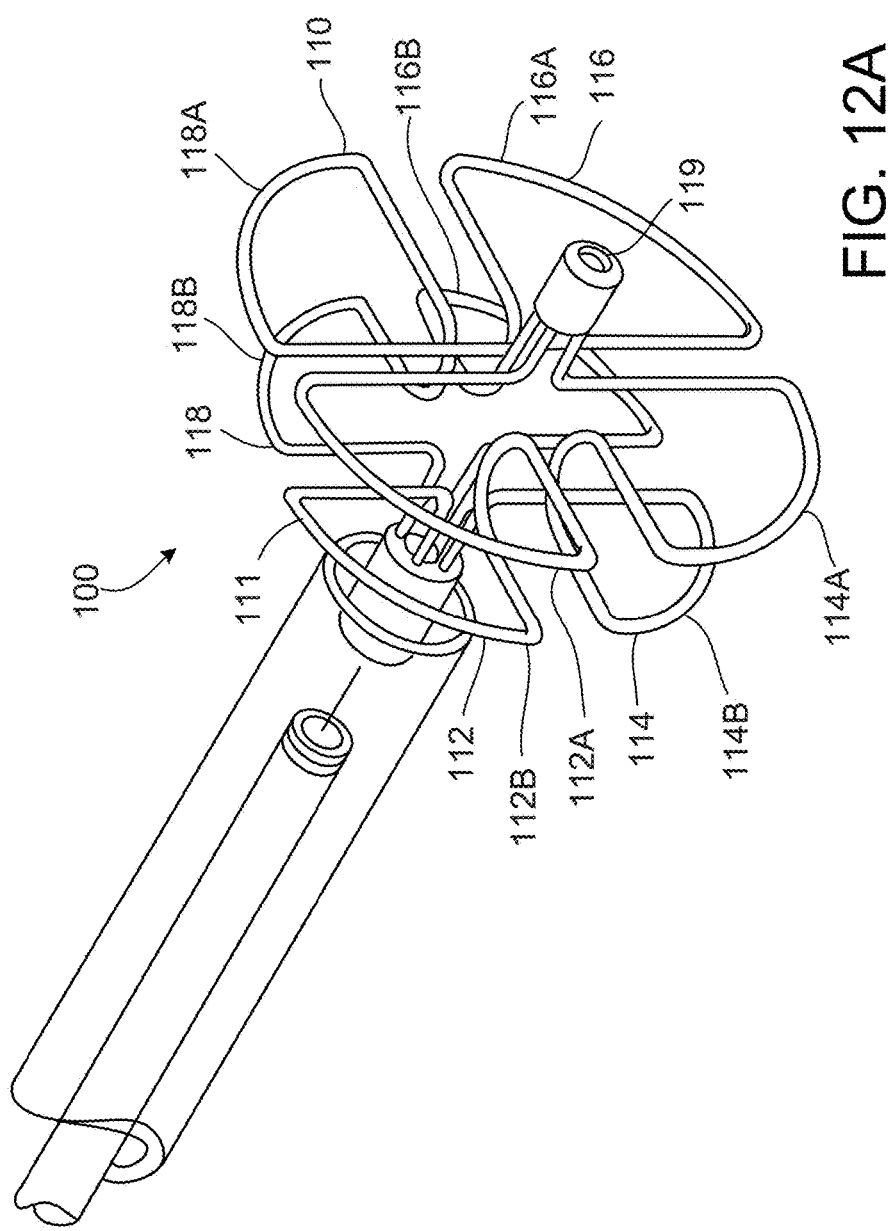

HEART OCCLUSION DEVICES

CROSS-REFERENCES TO RELATED APPLICATIONS

This is a divisional of U.S. patent application Ser. No. 15/086,449, filed Mar. 31, 2016, entitled HEART OCCLUSION DEVICES, now U.S. Pat. No. 9,474,517, issued Oct. 25, 2016, which is a continuation of U.S. patent application Ser. No. 13/772,801, filed Feb. 21, 2013, entitled HEART OCCLUSION DEVICES, now abandoned, which is a continuation-in-part of U.S. patent application Ser. No. 13/210,198, filed Aug. 15, 2011, entitled HEART OCCLUSION DEVICES, now U.S. Pat. No. 9,138,213, issued Sep. 22, 2015, which is a continuation-in-part of U.S. patent application Ser. No. 12/400,445, filed Mar. 9, 2009, entitled HEART OCCLUSION DEVICES, now U.S. Pat. No. 9,119,607, issued Sep. 1, 2015, which claims priority to U.S. Provisional Application No. 61/034,772, filed Mar. 7, 2008, entitled HEART OCCLUSION PLUG, all of which are incorporated herein by reference in their entireties.

FIELD OF THE INVENTION

The present invention is directed to a medical device and particularly to a device for closing congenital cardiac defects. The present invention is specifically directed to a heart occlusion device with a self-centering mechanism.

DESCRIPTION OF THE PRIOR ART

Heart occlusion devices for correcting congenital heart defects, such as atrial septal defects ("ASD"), patent foramen ovale ("PFO") defects, ventricular septal defects ("VSD"), and patent ductus arteriosus ("PDA") defects, are known to the medical field. The following companies manufacture different types of devices: AGA Medical, Microvena Corp./EV3 Medical, Velocimed/St. Jude Medical, Occlutech International, NMT Medical, Cardia, Inc., Solysafe S A, Sideris (Custom Medical, Inc.), W L Gore, and Cook, Inc.

A specific example of one such heart defect is a PFO. A PFO, illustrated in FIG. 1 at 6A, is a persistent, one-way, usually flap-like opening in the wall between the right atrium 2 and left atrium 3 of the heart 1. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 2 to the left atrium 3, and blood clots could enter the systemic circulation. It is desirable that this circumstance be eliminated.

The foramen ovale 6A serves a desired purpose when a fetus is gestating in utero. Because blood is oxygenated through the umbilical cord and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 8 and septum secundum 9. However, a PFO has been shown to persist in a number of adults.

The presence of a PFO defect is generally considered to have no therapeutic consequence in otherwise healthy adults. Paradoxical embolism via a PFO defect is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO defect and the risk for paradoxical embolism or stroke. In addition, there is significant evidence that patients with a PFO defect who have had a cerebral vascular event are at increased risk for future, recurrent cerebrovascular events.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO defect. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are not insignificant complications due to thrombus, fractures of the components, conduction system disturbances, perforations of heart tissue, and residual leaks. Many devices have high septal profile and include large masses of foreign material, which may lead to unfavorable body adaptation of a device. Given that ASD devices are designed to occlude holes, many lack anatomic conformability to the flap-like anatomy of PFOs. The flap-like opening of the PFO is complex, and devices with a central post or devices that are self-centering may not close the defect completely, an outcome that is highly desired when closing a PFO defect. Hence, a device with a waist which can conform to the defect will have much higher chance of completely closing the defect. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Devices for occluding other heart defects, e.g., ASD, VSD, PDA, also have drawbacks. For example, currently available devices tend to be either self-centering or non-self-centering and may not properly conform to the intracardiac anatomy. Both of these characteristics have distinct advantages and disadvantages. The non-self centering device may not close the defect completely and may need to be over-sized significantly. This type of device is usually not available for larger defects. Further, the self-centering device, if not sized properly, may cause injury to the heart.

Some have sharp edges, which may damage the heart causing potentially clinical problems.

Some devices contain too much nitinol/metal, which may cause untoward reaction in the patient and hence can be of concern for implanting physicians and patients.

Some currently marketed devices have numerous model numbers (several available sizes), making it difficult and uneconomical for hospitals and markets to invest in starting a congenital and structural heart interventional program.

The present invention is designed to address these and other deficiencies of prior art aperture closure devices. Furthermore, other desirable features and characteristics of the present invention will become apparent from the subsequent detailed description and the appended claims, taken in conjunction with the accompanying drawings and this section.

SUMMARY OF THE INVENTION

This document provides implantable occlusion devices and methods for occluding, for example, bodily apertures and channels. Some embodiments include frame elements, such as shape-memory wires, that are bent into patterns to form full and/or partial discs. Some embodiments are asymmetrical and include a full disc and a partial disc that are separated by a waist portion. Some embodiments include membranous coverings on the frame elements to enhance the occlusive properties of the device. Some embodiments include a self-centering feature.

Accordingly, one innovative aspect of the subject matter described in this specification may be embodied in a single-disc device for occluding an aperture within a body of a patient. The single-disc device comprises: an occluder region comprising a frame element, the frame element comprising a plurality of wire portions, the plurality of wire portions configured to form a disc at a first end of the single-disc device, wherein the disc generally defines a disc plane; an attachment region with an axis that extends transversely to the disc plane, the attachment region comprising an occluder region attachment end and a securing region attachment end, the occluder region attachment end being connected to the occluder region; and a securing region connected to the securing region attachment end and at a second end of the single-disc device, the securing region comprising one or more securing members, wherein a major axis of each of the one or more securing members extends transversely to the axis of the attachment region and all major axes of the one or more securing members are generally located within a circular sector having an arc of about 180 degrees or less.

In various implementations, the major axes of the securing members may be spaced symmetrically within the circular sector having an arc of about 180 degrees or less. The one or more securing members may each comprise one or more wire loops or wire prongs. The circular sector may have an arc of 150 degrees or less. The major axis of each of the one or more securing members may extend at an angle between 80 and 100 degrees with respect to the axis of the attachment region. The securing region may comprise three or more securing members. The disc plane may extend at an angle between 0 to 5 degrees with respect to the major axis of at least one of the one or more securing members. The disc plane may extend at an angle between 5 to 15 degrees with respect to the major axis of at least one of the one or more securing members. The occluder region may comprise a membrane configured to inhibit passage of blood, wherein the membrane covers at least a portion of the disc. The membrane may comprise a fluoropolymer. The membrane may comprise polytetrafluoroethylene. The membrane may comprise expanded polytetrafluoroethylene. The occluder region may further comprise an expandable balloon configured to restrict fluid flow through the aperture. The occluder region may comprise at least one anchor. The single-disc device may comprise one or more visual indicators configured to identify the orientation of the securing region. The disc plane may extend at an angle between 75 to 105 degrees with respect to the axis of the attachment region. The first end may be at the proximal end of the single-disc device, and the second end may be at the distal end of the single-disc device.

Another innovative aspect of the subject matter described in this specification may be embodied in a method of occluding a cardiac defect. The method comprises: providing a single-disc device; configuring the single-disc device in a delivery configuration and advancing the single-disc device to a delivery site; and deploying the single-disc device at the delivery site. The single-disk device comprises: an occluder region comprising a frame element, the frame element comprising a plurality of wire portions, the plurality of wire portions configured to form a disc at a first end of the single-disc device, wherein the disc generally defines a disc plane; an attachment region with an axis that extends transversely to the disc plane, the attachment region comprising an occluder region attachment end and a securing region attachment end, the occluder region attachment end being connected to the occluder region; and a securing region connected to the securing region attachment end and at a second end of the single-disc device, the securing region comprising one or more securing members, wherein a major axis of each of the one or more securing members extends transversely to the axis of the attachment region and all major axes of the one or more securing members are generally located within a circular sector having an arc of 180 degrees or less.

In various implementations, the method may further comprise coupling the single-disc device to a delivery catheter. The method may further comprise inserting the single-disc device and the delivery catheter into a delivery sheath. The frame element may collapse as the single-disc device is inserted into the delivery sheath. Deploying the single-disc device may comprise advancing the single-disc device through the delivery sheath such that at least a portion of the single-disc device exits the delivery sheath distal of the delivery sheath. The frame element may expand as the single-disc device exits the delivery sheath. Deploying the single-disc device may comprise pulling the delivery sheath away from the cardiac defect while maintaining a position of the single-disc device. Deploying the single-disc device may substantially occlude the cardiac defect.

Another innovative aspect of the subject matter described in this specification may be embodied in a system for occluding an aperture within a body of a patient. The system comprises: a single-disc occluder device; a deployment wire releasably attached to the first end of the single-disc device; a delivery catheter comprising a sheath configured to contain the deployment wire and the single-disc occluder device arranged in a delivery configuration, the delivery catheter configured to advance the single-disc device to a delivery site; and an actuator device attached to a proximal end of the delivery catheter, the actuator device being configured to remotely control deployment of the single-disc device at the delivery site. The single-disc device comprises: an occluder region comprising a frame element, the frame element comprising a plurality of wire portions, the plurality of wire portions configured to form a disc at a first end of the single-disc device, wherein the disc generally defines a disc plane; an attachment region with an axis that extends transversely to the disc plane, the attachment region comprising an occluder region attachment end and a securing region attachment end, the occluder region attachment end being connected to the occluder region; and a securing region connected to the securing region attachment end and at a second end of the single-disc device, the securing region comprising one or more securing members, wherein a major axis of each of the one or more securing members extends transversely to the axis of the attachment region and all major axes of the one or more securing members are generally located within a circular sector having an arc of 180 degrees or less.

Another innovative aspect of the subject matter described in this specification may be embodied in a method of occluding a blood vessel. The method comprises: providing a single-disc device; configuring the single-disc device in a delivery configuration and advancing the single-disc device to a delivery site in the vessel; and deploying the single-disc device at the delivery site in the vessel. The single-disc device comprises: an occluder region comprising a frame element, the frame element comprising a plurality of wire portions, the plurality of wire portions configured to form a disc at a first end of the single-disc device, wherein the disc generally defines a disc plane; an attachment region with an axis that extends transversely to the disc plane, the attachment region comprising an occluder region attachment end and a securing region attachment end, the occluder region attachment end being connected to the occluder region; and a securing region connected to the securing region attachment end and at a second end of the single-disc device, the securing region comprising one or more securing members, wherein a major axis of each of the one or more securing members extends transversely to the axis of the attachment region and all major axes of the one or more securing members are generally located within a circular sector having an arc of 180 degrees or less.

In various implementations, the method may further comprise coupling the single-disc device to a delivery catheter; inserting the single-disc device and the delivery catheter into a delivery sheath, wherein the frame element collapses as the single-disc device is inserted into the delivery sheath, and wherein the frame element expands as the single-disc device exits the delivery sheath. Deploying the single-disc device may comprise advancing the single-disc device through the delivery sheath, such that at least a portion of the single-disc device exits the delivery sheath distal of the delivery sheath.

The device of the present invention has many advantages:

Lower Profile: The occluder device of the present invention has a lower profile than available devices.

Conformable: The device is flexible and conformable to the patient anatomy, specifically the hole that is being closed. There are no sharp edges. The device is soft and hence less traumatic to the atrial tissue.

Self-Centering on Demand: Because of the unique way the two discs are connected, the device has self-centering characteristics. The uniqueness of this device is in the self-centering mechanism. In some embodiments, the waist of the device is made of four wires. In some embodiments, the waist of the device can be made of fewer than or more than four wires. The wires will have the capability to conform to the shape and size of the defect in the organ—a characteristic not seen in prior art devices. Therefore, the self-centering of the device is dependent upon the size and the shape of the defect. The wires will have enough radial force to maintain the self-centering configuration but will not be strong enough to press against the defect edges in a manner that exacerbates the defect. The device is fully repositionable and retrievable after deployment.

Custom Fit: The device has the further ability to be custom-fit within the defect using, for example, balloon-expansion of the waist. Because of the self-expanding nature of the waist, this will not be needed in most cases. However, in some cases in which custom expansion is needed (oval defects, tunnel defects), the waist size can be increased to conform to the defect by the balloon catheter expansion, or another suitable method. A balloon may be inserted through a hollow screw attachment on the device's delivery hub and delivery cable. The expansion will be possible before the release of the device, which will increase the margin of safety.

Fewer Sizes: The expandable waist requires fewer sizes to close a wider variety of differently-sized defects. Thus, a single device may offer physicians the ability to implant devices in several different sizes.

The device will be less thrombogenic as the discs will be covered with ePTFE. The ePTFE has been time-tested and found to be least thrombogenic. There is the ability to close defects up to 42 mm with very mild modifications.

Security: There will be the opportunity to remain tethered to the implanted device before releasing it, which is an extra security feature.

Uses:

The device of the present invention should be appropriate for an ASD (atrial septal defect), PFO (patent foramen ovale), VSD (ventricular septal defect), and PDA (patent ductus arteriosus) with minor modifications. One skilled in the art would also recognize the device's application for use as a vascular occluder or plug as well as an atrial appendage occluder.

An important use of the device will also be in closure of an aperture in a left atrial appendage. The device can be modified to conform to the atrial appendage anatomy. The discs are modified so that the device is not extruded out with the heartbeats. Yet, the device is still soft enough to form adequate closure.

The discs can also be modified so that they become compatible for closure of veins and arteries. For this use, the connecting waist will become equivalent (or near equivalent) to the diameter of the discs. Other important uses will be in closure of coronary artery fistulas, arteriovenous fistulas, arteriovenous malformations, etc.

The objects and advantages of the invention will appear more fully from the following detailed description of the preferred embodiments of the invention made in conjunction with the accompanying drawings.

BRIEF DESCRIPTION OF THE DRAWINGS

FIG. 12A is a perspective view of a first alternative embodiment of the occluder device of the present invention.

DETAILED DESCRIPTION OF THE INVENTION

The following detailed description is merely exemplary in nature and is not intended to limit the disclosure or the application and uses of the disclosure. Furthermore, there is no intention to be bound by any theory presented in the preceding background information or the following detailed description.

The present invention provides a device for occluding an aperture within body tissue. One skilled in the art will recognize that the device and methods of the present invention may be used to treat other anatomical conditions in addition to those specifically discussed herein. As such, the invention should not be considered limited in applicability to any particular anatomical condition.

Figure 1:
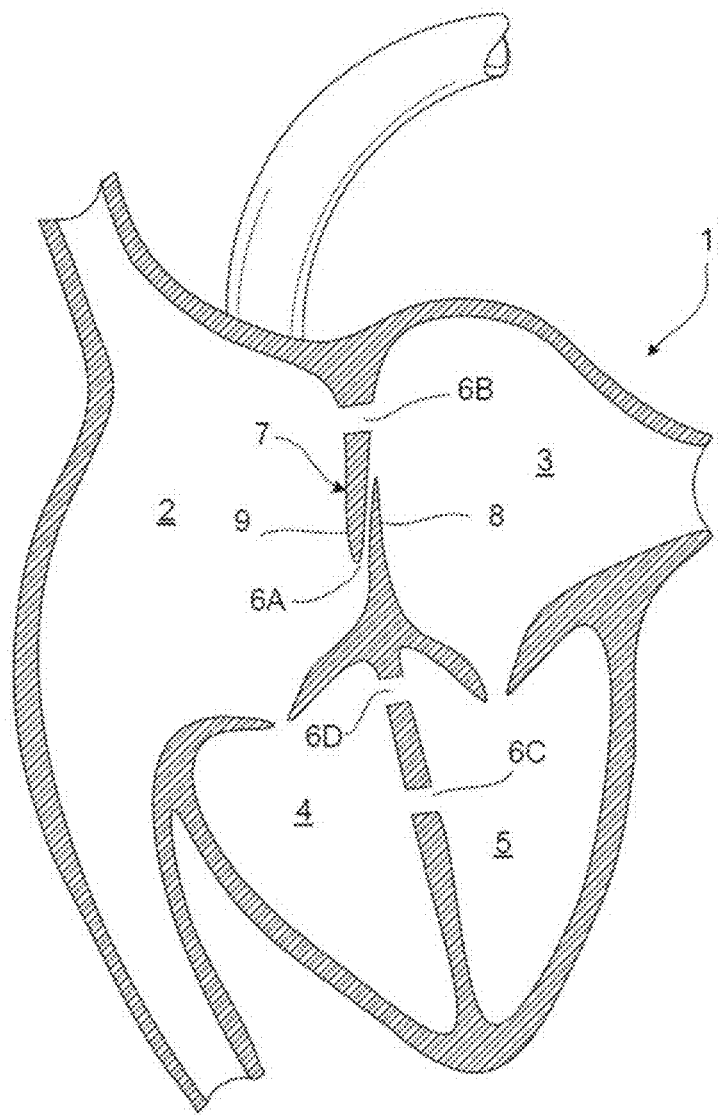
FIG. 1 is a schematic representation of a human heart including various septal defects.

FIG. 1 illustrates a human heart 1, having a right atrium 2, a left atrium 3, a right ventricle 4, and a left ventricle 5. Shown are various anatomical anomalies 6A, 6B, and 6C. The atrial septum 7 includes septum primum 8 and septum secundum 9. The anatomy of the septum 7 varies widely within the population. In some people, the septum primum 8 extends to and overlaps with the septum secundum 9. The septum primum 8 may be quite thin. When a PFO is present, blood could travel through the passage 6A between septum primum 8 and septum secundum 9 (referred to as "the PFO tunnel"). Additionally or alternatively, the presence of an ASD could permit blood to travel through an aperture in the septal tissue, such as that schematically illustrated by aperture 6B. A VSD is similar to an ASD, except that an aperture 6C exists in the septum between the left and right ventricle of the heart.

PDA results from defects in the ductus arteriosus. The human blood circulation comprises a systemic circuit and a pulmonary circuit. In the embryonic phase of human development, the two circuits are joined to one another by the ductus arteriosus. The ductus connects the aorta (circulation to the body) to the pulmonary artery (pulmonary circuit). In normal development of an infant, this ductus closes after birth. If development is defective, it can happen that the ductus does not close, and as a result the two blood circuits are still joined even after birth.

Unless specifically described otherwise, "aperture" 6 will refer to the specific heart defects described above, including PFO 6A, ASD 6B, VSD 6C, perimembranous VSD 6D, and PDA among others.

As used herein, "distal" refers to the direction away from a catheter insertion location and "proximal" refers to the direction nearer the insertion location.

As used herein, "left" refers to the left chambers of the heart, including the left atrium and left ventricle. "Right" refers to the right chambers of the heart, including the right atrium and right ventricle.

As used herein, "superior" refers to the direction toward the head of the patient and "inferior" refers to the direction toward the feet of the patient.

As used herein, "memory" or "shape memory" refers to a property of materials to resume and maintain an intended shape despite being distorted for periods of time, such as during storage or during the process of delivery in vivo.

Referring now to FIGS. 2-5, the occluder device 10 of the present invention comprises two separate uniquely shaped memory wires 12, 14. The wire can be formed of biocompatible metals or polymers, such as bioresorbable polymers, shape memory polymers, shape memory metal alloys, biocompatible metals, bioresorbable metals, or combinations thereof. Specific examples include but are not limited to iron, magnesium, stainless steel, nitinol, or combinations of these and similar materials. A preferred metal for the present invention is a nitinol alloy. Nitinol (an acronym for Nickel Titanium Naval Ordnance Laboratory) is a family of inter-metallic materials, which contain a nearly equal mixture of nickel (55 wt. %) and titanium. Other elements can be added to adjust or "tune" the material properties. Nitinol exhibits unique behavior, specifically, a well defined "shape memory" and super elasticity. In general, any biocompatible material with a memory capability can be used with the present invention. The thermal shape memory and/or super-elastic properties of shape memory polymers and alloys permit the occluder 10 to resume and maintain its intended shape in vivo despite being distorted during the delivery process. In certain embodiments, the memory may also assist in pressing an aperture, such as a PFO tunnel, closed. The diameter or thickness of the wire depends on the size and type of the device, i.e., the larger the device, the larger the diameter of the wire. In general, wire having a diameter between about 0.2 mm and 0.8 mm can be used. As described further below in connection with FIGS. 12A, 12B, and 22, in certain embodiments more than two wires may be utilized.

The first wire 12 forms one or more first geometric forms 12A and one or more second geometric forms 12B. "Geometric forms" as used herein comprises symmetric as well as asymmetric forms. Relative to a delivery attachment mechanism or hub 30, discussed below in greater detail, the first geometric form 12A of the first wire 12 preferably comprises a distal geometric form, and the one or more second geometric forms 12B of the first wire preferably each comprise proximal geometric forms. In the embodiment of FIGS. 2-5, there is a single first, or distal, geometric form 12A of the first wire 12. Also in the embodiment of FIGS. 2-5, there are two second, or proximal, geometric forms 12B of the first wire 12 (namely, 12B(A) and 12B(B)). However, the number and configuration of the first and/or second geometric forms 12A, 12B of the first wire 12 may vary.

Similarly, the second wire 14 forms a first geometric form 14A and a second geometric form 14B. Relative to the hub 30, the first geometric form 14A of the second wire 14 preferably comprises a distal geometric form, and the second geometric form 14B of the second wire preferably comprises a proximal geometric form. In the embodiment of FIGS. 2-5, there is a single first, or distal, geometric form 14A of the second wire 14. Also in the embodiment of FIGS. 2-5, there are two second, or proximal, geometric forms 14B of the second wire 14 (namely, 14B(A) and 14B(B)). However, the number and configuration of the first and/or second geometric forms 14A, 14B of the second wire 14 may vary.

The first geometric forms 12A of the first wire 12 and the first geometric forms 14A of the second wire 14 form a first plate, such as a disc, or another otherwise relatively flat surface (hereinafter referred to as a "plate") 16 in a first plane 218. The second geometric forms 12B of the first wire 12 and the second geometric forms 14B of the second wire 14 form a second plate 18 (also referred to as a "disc" in certain embodiments) in a second plane 220 that is parallel to and remote from the first plane 218. In the embodiment of FIGS. 2-5, the first and second plates 16, 18 each comprise one or more semi-circular discs (as described directly below). However, this may vary in some embodiments, for example as described further below in connection with FIGS. 21A-21E.

As shown in FIGS. 2-5, in these embodiments, each wire 12 or 14 forms a shape which mirrors that of the respective wire 14 or 12. Specifically, each wire 12, 14 forms a distal semi-circle or half-disc 12A, 14A in addition to two proximal quarter-circles or quarter-discs 12B, 12B' or 14B, 14B'. The two proximal quarter-circles of each wire together form proximal semi-circles or half-discs 12B, 12B' or 14B, 14B'. The two distal semi-circles of each respective wire 12A, 14A together comprise a distal circle or distal disc 16 of the occluder 10. The four proximal quarter-circles 12B, 12B', 14B, 14B', which form a "four-leaf clover" configuration, comprise a proximal circle or proximal disc 18 of the occluder 10.

Figure 2:
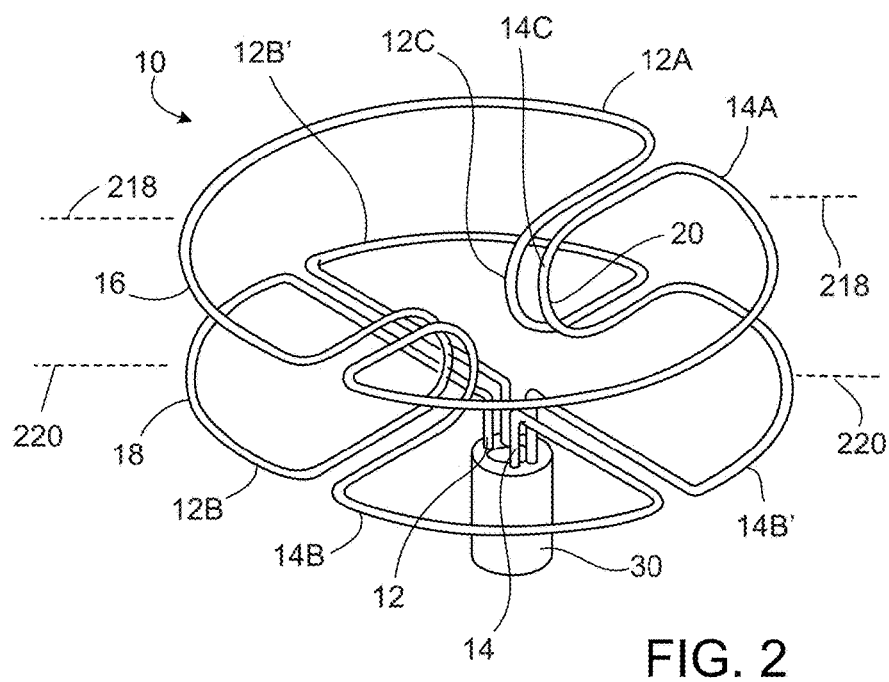
FIG. 2 is a perspective view of the occluder device of the present invention.
Figure 3:
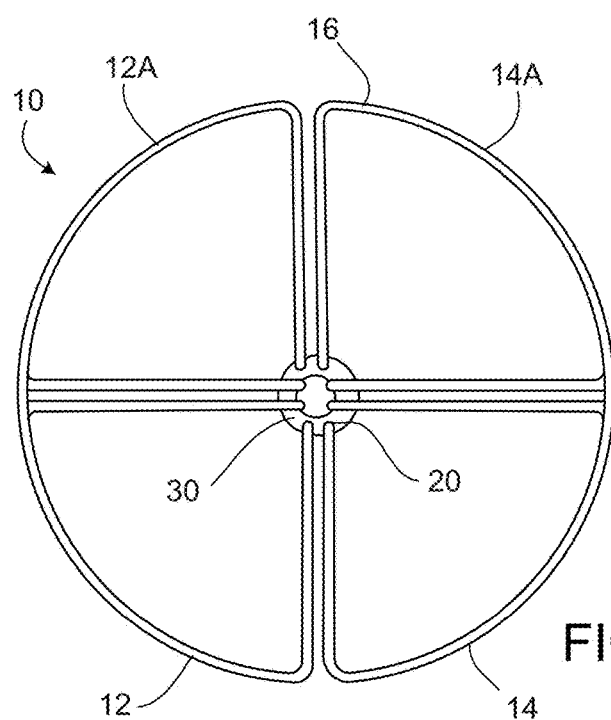
FIG. 3 is a top plan view of the occluder device of FIG. 2.
Figure 4:
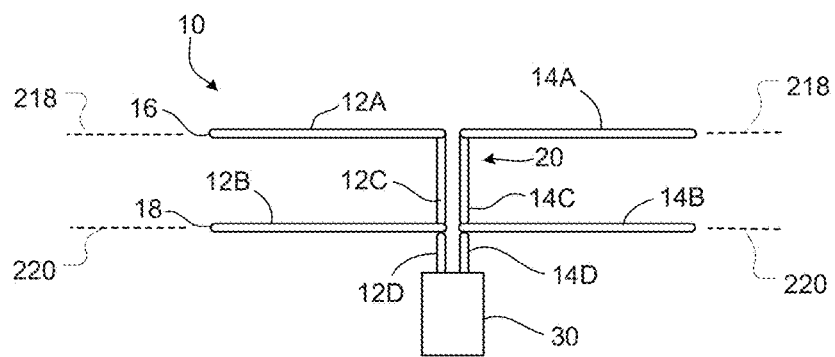
FIG. 4 is a side plan view of the occluder device taken along lines in FIG. 2.
Figure 5:
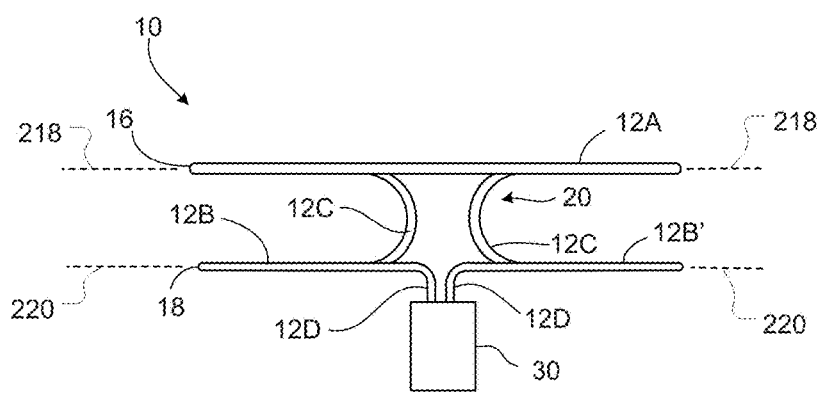
FIG. 5 is a side plan view of the occluder device taken along in FIG. 2.

The proximal semi-circle 12B, 12B' or 14B, 14B' of each wire is connected to the distal semi-circle 12A or 14A by waist portions (also referred to herein as waist components) 12C, 14C. As shown in FIG. 2, there are two waist portions 12C, 14C per wire. The four waist portions (two from each wire) 12C, 14C together comprise a restricted area or waist 20 of the occluder device 10. The distance between the waist portions, both within the same wire and from wire to wire, determines the size of the waist 20. The size of the waist 20 is dependent on the particular application and the size of the occluder device 10. The resiliency and memory of the waist portions 12C, 14C and capacity to expand radially serves as a self-centering mechanism of the occluder device 10 in apertures 6.

The Hub 30:

The two half-discs are not attached or joined to each other except at the junction of the delivery attachment mechanism or hub 30. The ends 12D, 14D of wires 12, 14 will be welded or otherwise connected to the hub 30.

Figure 6:
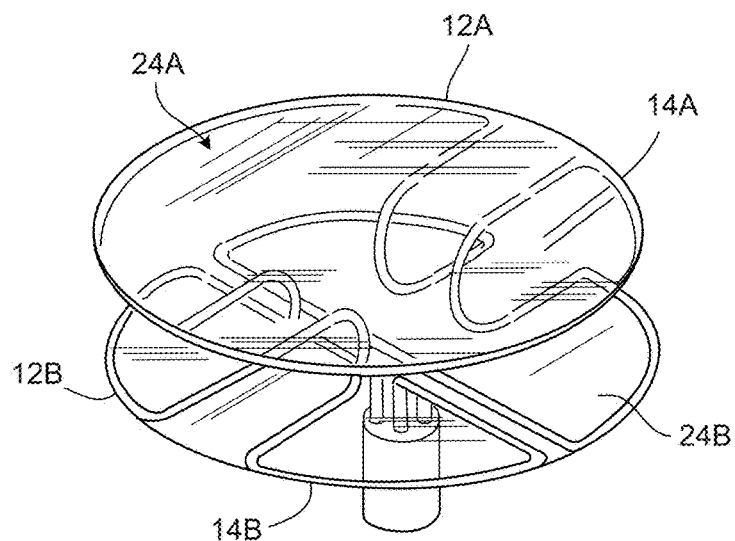
FIG. 6 is a perspective view of the occluder device of FIG. 2, illustrating the covering 42.
Figure 7:
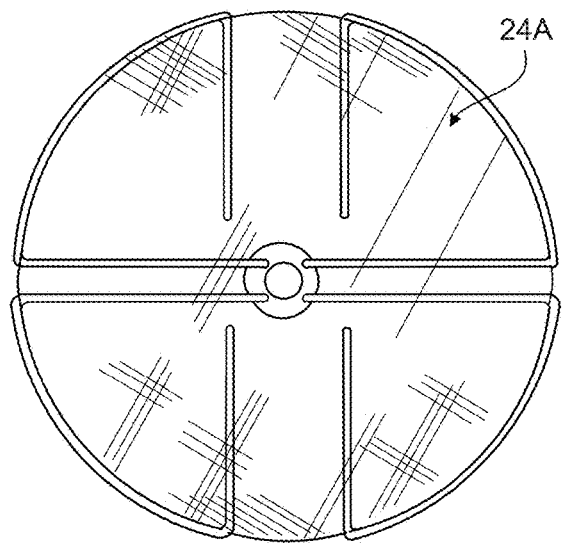
FIG. 7 is a top plan view of the occluder device of FIG. 6.

Coverings 24A and 24B:

According to some embodiments of the present invention, the distal disc 16 and/or proximal disc 18 may include membranous coverings 24A and 24B, illustrated in FIGS. 6 and 7. The membranous coverings 24A and 24B ensure more complete coverage of aperture 6 and promote encapsulation and endothelialization of tissue, thereby further encouraging anatomical closure of the tissue and improving closure rate. The coverings 24A and 24B also help stabilize the occluder device 10.

The membranous coverings 24A and 24B may be formed of any flexible, biocompatible material capable of promoting tissue growth and/or act as a sealant, including but not limited to DACRON.RTM., polyester fabrics, Teflon-based materials, ePTFE, polyurethanes, metallic materials, polyvinyl alcohol (PVA), extracellular matrix (ECM) or other bioengineered materials, synthetic bioabsorbable polymeric materials, other natural materials (e.g. collagen), or combinations of the foregoing materials. For example, the membranous coverings 24A and 24B may be formed of a thin metallic film or foil, e.g. a nitinol film or foil, as described in U.S. Pat. No. 7,335,426 (the entirety of which is incorporated herein by reference). The preferred material is Poly(tetrafluoroethene) (ePTFE), as it combines several important features such as thickness and the ability to stretch. Loops may also be stitched to the membranous coverings 24A and 24B to securely fasten the coverings to occluder 10. The coverings may alternatively be glued, welded or otherwise attached to the occluder 10 via the wires 12, 14.

Size:

As illustrated in FIGS. 2-7, the diameters of the distal disc 16 and proximal disc 18 are generally 5-8 mm larger than the diameter of the connecting waist 20. For example, if the diameter of the connecting waist 20 is 4 mm, the diameters of the discs 16, 18 are generally about 9 mm each. Because of the flexibility in the waist 20, a 12 mm waist device will be able to be placed in a 6 mm to 12 mm defect. For larger waists 20 or larger devices, the diameter of the disc size will increase proportionately.

It is within the scope of the present invention to envision occluder devices available in 7 or more sizes, specifically waist size having the following diameters for different-sized apertures 6: 6 mm, 12 mm, 18 mm, 24 mm, 30 mm, 36 mm, and 42 mm. Occluder devices having waist size to fit other aperture sizes are also contemplated.

Operation:

In general, the occluder 10 may be inserted into an aperture 6 to prevent the flow of blood therethrough. As a non-limiting example, the occluder 10 may extend through a PFO 6A or an ASD 6B such that the distal disc 16 is located in the left atrium 3 and the proximal disc 18 is located in the right atrium 2 (as shown in the heart 1 in FIG. 1). The closure of apertures in these and other tissues, as well as other types of apertures, will become apparent as described below.

Figure 8:
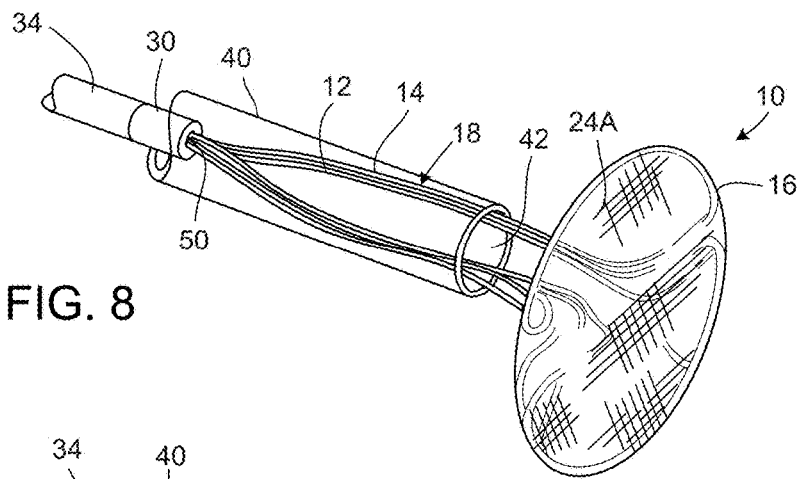
FIG. 8 is a perspective view of the occluder device first emerging from the catheter.
Figure 9:
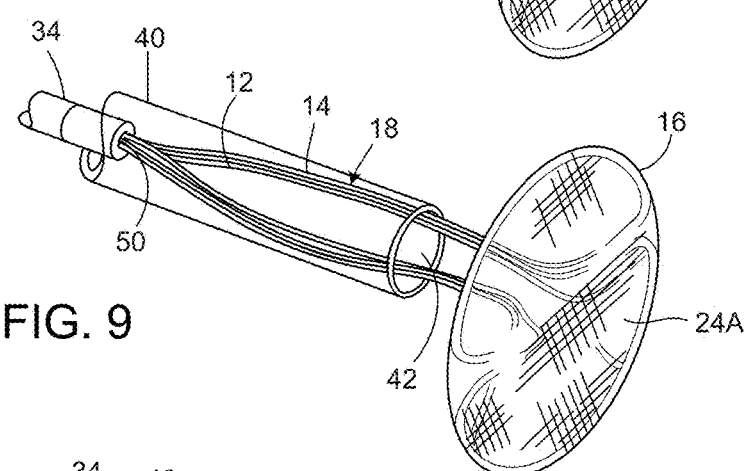
FIG. 9 is a perspective view of the occluder device half-way emerged from the catheter.
Figure 10:
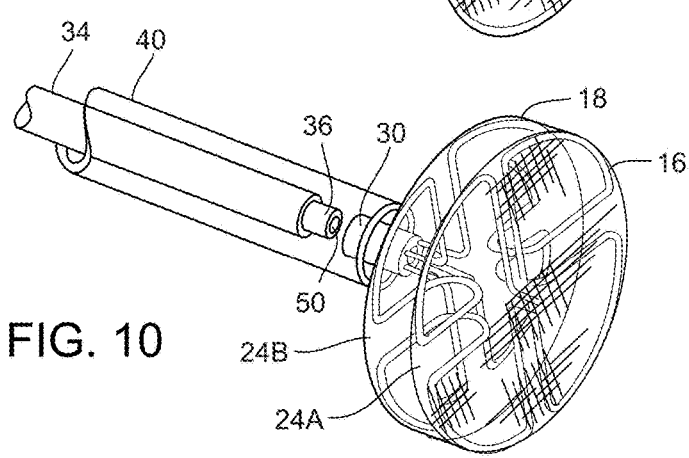
FIG. 10 is a perspective view of the occluder device fully emerged from the catheter and separated from the deployment cable.

Referring now to FIGS. 8-10, the occluder device 10 is attached to a deployment cable 34 which is removably attached to the occluder device 10 at the hub 30. As illustrated in FIG. 10, one method of releasably attaching the deployment cable 34 to the hub 30 is by threaded engagement utilizing a screw end 36 which engages unseen female threads within the hub 30. Other known means of attachment can be used to releasably connect the deployment cable 34 to the hub 30.

When the deployment cable 34 is engaged with the hub 30, as illustrated in FIGS. 8 and 9, the occluder device 10 is initially housed within a flexible delivery catheter 40 having an open channel 42. Reference is made to FIG. 8 which illustrates the occluder device 10 in which the distal disc 16 is expanded, due to the memory expansion of the wires 12 and 14, and housed within the open channel 42 of the delivery catheter 40. During the initial stages of placement of the occluder device 10, both the distal disc 16 and proximal disc 18, as well as the coverings 24A and 24B, are housed within the open channel 42 of the delivery catheter 40. In this manner, the catheter 40 is fed into the blood vessel through an already placed sheath and advanced via the blood vessel system to a defect in the heart.

Once the delivery catheter 40 traverses the aperture that needs to be occluded, e.g., a hole in the heart, the device 10 will be partially advanced from the catheter 40 as illustrated in FIG. 8. As the device 10 leaves the catheter 40, the distal disc 16, which includes the covering 24A, begins to expand on the distal side of the aperture. Due to the memory capabilities of the wires 12 and 14, the occluder device 10 begins to return to its normal shape such that the distal disc 16 expands on the distal side of the aperture in the heart. Once the distal disc 16 is completely out of the catheter opening 42, as shown in FIG. 9, it 16 and the attached covering 24A become fully expanded. The catheter 40 is further withdrawn to expose the waist 20 which then begins to emerge and expand due to the memory shape of the wires 12 and 14. Advantageously, the waist 20 is designed to expand such that each of the wires forming the waist 20 are urged against the aperture in the heart causing a custom fit device of the occluder 10 within the aperture. As the catheter 40 is further withdrawn, the proximal disc 18 and the covering 24B begin their process of expansion on the proximal side of the aperture. When the proximal disc 18 is fully delivered from the catheter 40, it will expand and effectively form a seal over the aperture. The distal disc 16 and proximal disc 18 are secured in place by the action of the wires in the waist 20 urging against the aperture. At this stage, as shown in FIG. 10, the deployment cable 34 is removed from the hub 30 and the catheter 40 and the deployment cable 34 are removed from the body. The occluder device 10 is left in the heart at the region of the aperture. Over several months, cardiac tissue and other membranous structures will bind to the occluder device 10 thereby permanently locking the occluder device 10 to the specific area in the heart.

The two wires 12, 14 function to form round discs 16, 18 on each side of the tissue. The discs 16, 18 maintain the circular shape because of the memory capability of the wires 12, 14. The coverings 24A, 24B will stabilize the discs and will act to completely occlude the defect.

The wires 12, 14 at the waist portions 12C, 14C will be separated enough at the waist 20 to make the occluder device 10 self-centering. Due to the conformity of this design, the occluder device 10 can self-center within commonly (round, oval) shaped septal defects, as the waist 20 can adjust to any type of opening.

If a larger-diameter waist 20 is required, the waist 20 has the capability to expand (only if needed) to a larger size with the help of a balloon. In this manner, a center channel 50 extends through the deployment cable 34, the hub 30, and the screw end 36. A balloon (not shown) is urged through the center channel 50 after the occluder device has been removed from the catheter 40 and expanded, and preferably before the hub 30 has been attached from the deployment cable 34. The balloon is placed within the waist 20 and expanded. The waist 20 is dilatable, i.e., expandable, when gentle pressure of the balloon is applied. The dilation will expand the waist portions 12C, 14C. Once the desired diameter is reached, the balloon is deflated and removed by withdrawal through the center channel 50. Once the occluder device 10 appears stable, the device 10 is separated from the deployment cable 34 as discussed above. In the majority of cases, balloon dilation will not be required.

Figure 11:
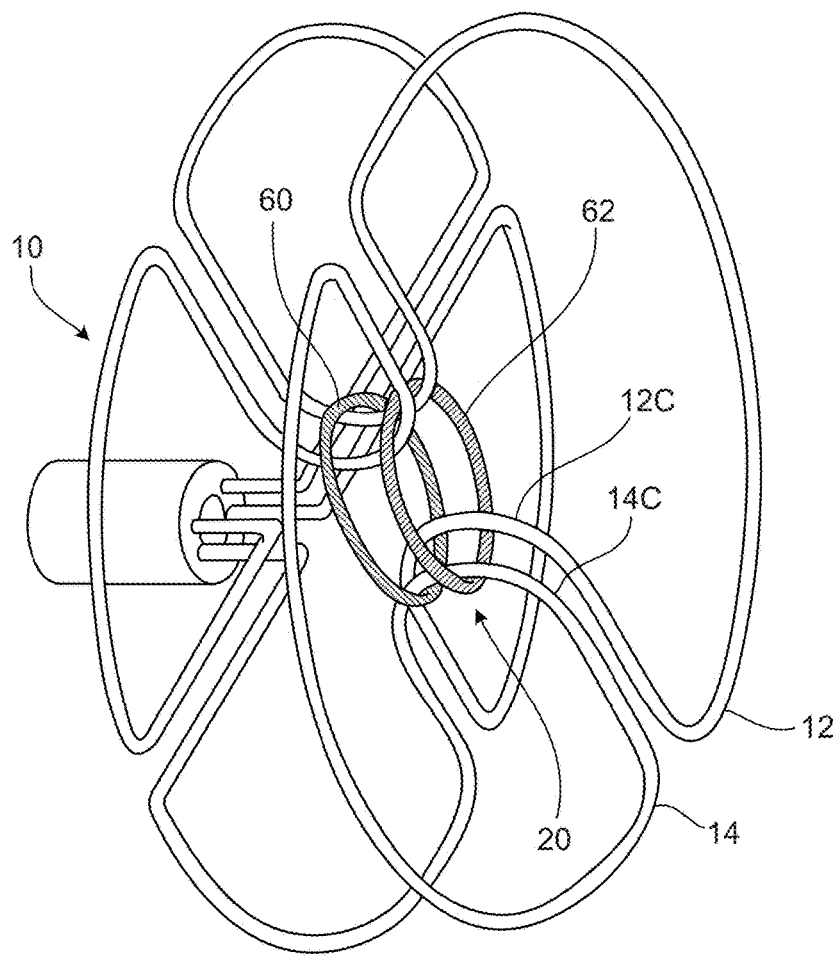
FIG. 11 is a perspective view of the occluder device of the present invention illustrating restriction wires encircling the waist of the occluder device.

Restriction Wires 60, 62 (FIG. 11):

In order to increase stability in the occluder device 10 and to avoid significant crimping of the waist 20 or the proximal or distal discs 18, 16, the waist 20 can be encircled by one or more restriction wires 60, 62 as illustrated in FIG. 11. The restriction wires 60, 62 can be made of the same wire material as the wires 12 and 14, or they may be of a different material, such as plastic wire, fish line, etc. The restriction wires 60, 62 may be welded or otherwise connected to the waist portions 12C, 14C. The purpose of the restriction wires 60 or 62 is also to restrict the circumference of the waist 20 if necessary. Although one restriction wire 60 is generally suitable, a second restriction wire 62 can also be incorporated to further improve stability.

Alternative Embodiments:

Reference is now made to FIGS. 12-15 for alternative embodiments of the occluder device 10 of the present invention. Unless otherwise noted, the same reference numbers will be applied to similar structures in each embodiment.

Figure 12B:
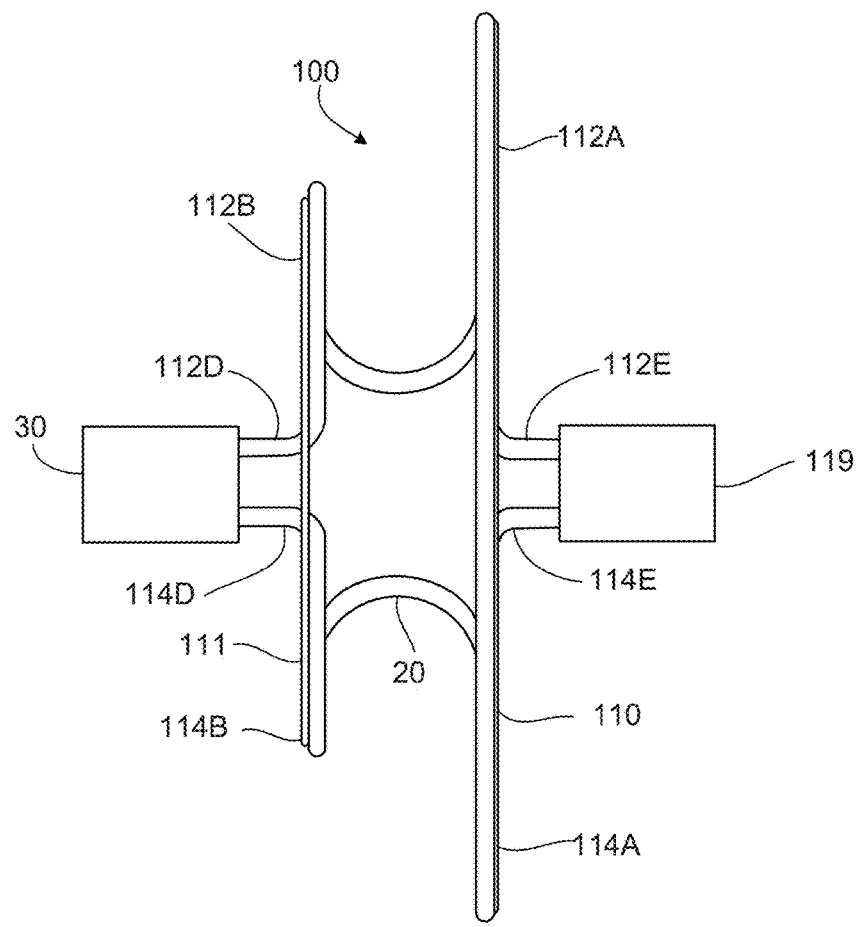
FIG. 12B is a side plan view of the first alternative embodiment of the occluder device of the present invention as shown in FIG. 12A.

Reference is made to FIGS. 12A and 12B for an alternative embodiment of the occluder device (labeled as occluder device 100 in FIGS. 12A and 12B). The occluder device 100 in this embodiment is designed for PDA procedures. This embodiment is similar to previously described embodiments except that it is comprised of four wires 112, 114, 116, 118 rather than two wires. In this case, each wire forms a mirror image of each of its neighboring wires. For example, wire 112 mirrors wire 114 as well as wire 118, etc. Each of the four wires 112, 114, 116, 118 forms a proximal quarter-disc 112B, 114B, 116B, 118B and a distal quarter-disc 112A, 114A, 116A, 118A. The proximal quarter-discs 112B, 114B, 116B, 118B together form a proximal disc 111 in a "four-leaf clover" configuration, and the distal quarter-discs 112A, 114A, 116A, 118A together form a distal disc 110 also in a "four-leaf clover" configuration. This embodiment also differs from previously-described embodiments in that the waist 20 is comprised of a single portion of each of the four wires 112, 114, 116, 118. This embodiment further differs from previously-described embodiments in that it comprises a second hub 119 with a screw mechanism. The second hub 119 connects to the distal disc 110 by distal ends 112E, 114E (116E, 118E behind 112E, 114E in FIG. 12B) of each of the four wires 112, 114, 116, 118, just as proximal ends 112D, 114D (116D, 118D behind 112D, 114D in FIG. 12B) connect to the proximal hub 30. The wires 112, 114, 116, 118 may be connected to the hubs 30, 119 by welding or other means known in the art. The length of the waist 20 will be anywhere from 4-8 mm. In addition, the distal disc 110 is typically 4-8 mm larger than the waist 20. However, the proximal disc 111 is generally 1-3 mm, preferably 2 mm, larger than the waist 20 diameter. Hence, the diameter of the distal disc 110 is larger than the diameter of the proximal disc 111.

Figure 13:
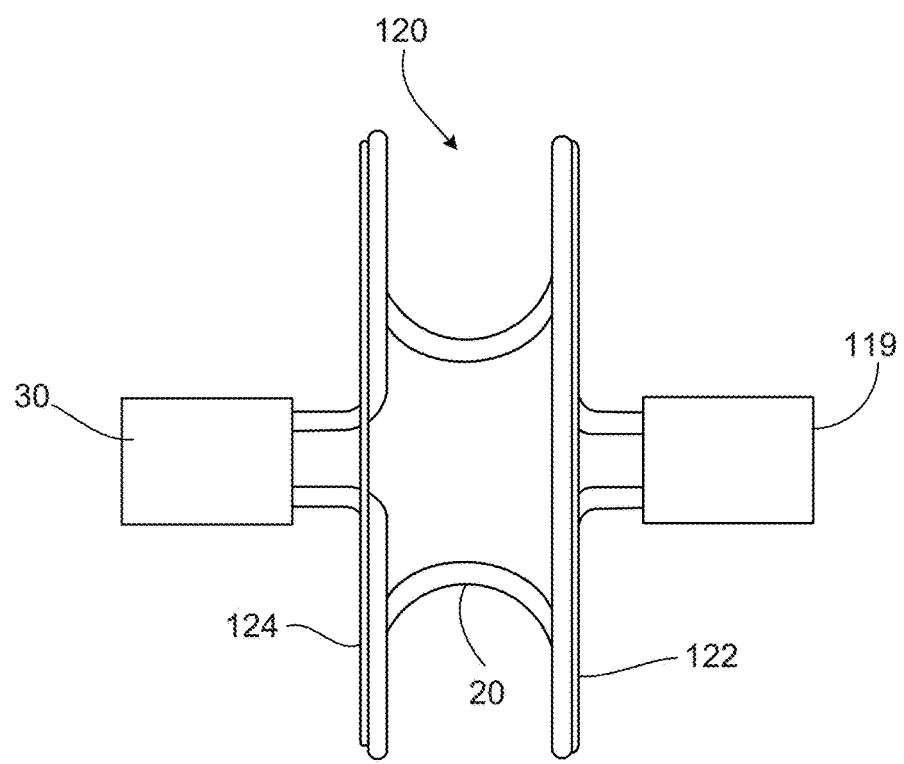
FIG. 13 is a side plan view of a second alternative embodiment of the occluder device of the present invention.

Reference is now made to FIG. 13 for a second alternative embodiment of the occluder device 120. This embodiment, like the embodiment shown in FIGS. 12A and 12B, uses four wires 112, 114, 116, 118 and two hubs 30, 119. It is designed to close apertures in large arteries and veins. In occluder device 120, the distal and proximal discs 122 and 124 are modified so that they are compatible with closure of veins and arteries. For this use, the connecting waist 20 is equivalent or near equivalent to the diameter of each of the discs 122, 124. The diameter of the waist 20 will be 1 mm smaller than the discs 122, 124. The length of the waist will be 4-8 mm. This embodiment can be used in the closure of coronary artery fistulas, arteriovenous fistulas, and arteriovenous malformations.

Figure 14:
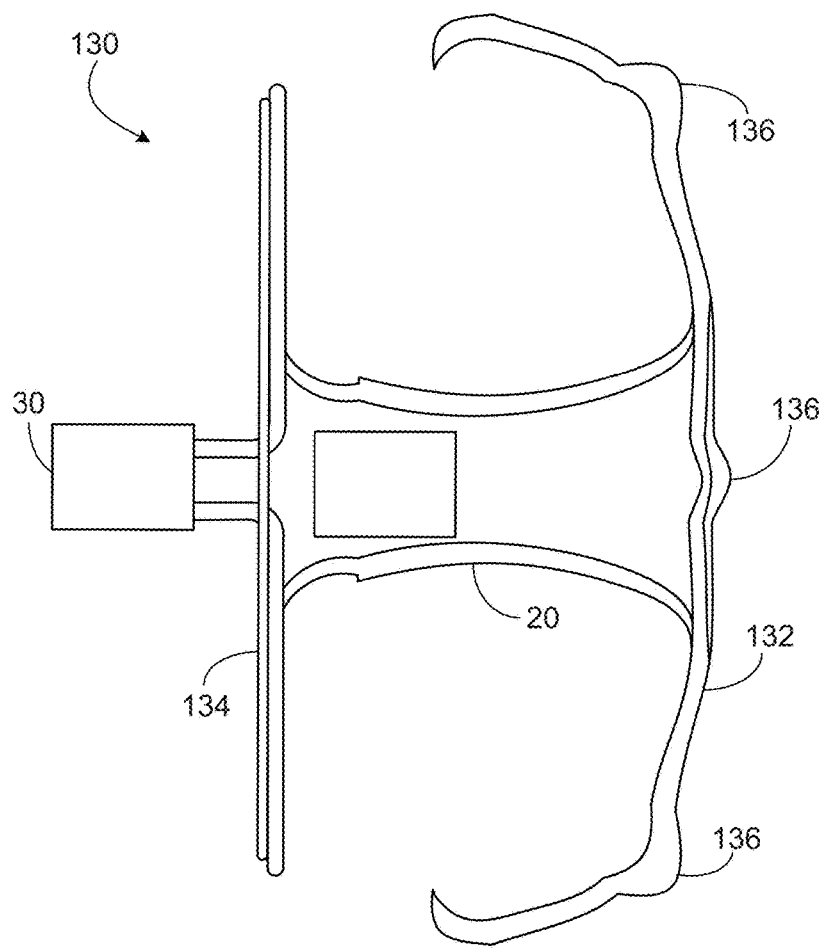
FIG. 14 is a side plan view of a third alternative embodiment of the occluder device of the present invention.

Reference is made to FIG. 14 for a third alternative embodiment of the occluder device 130. The importance of the occluder device 130 will be in the closure of the left atrial appendage. The device 130 is modified to conform to the atrial appendage anatomy. The distal disc 132 is modified so that the device 130 is not extruded out with the heartbeats. For the left atrial appendage occluder device 130, the memory wire structure of the distal disc 132 is woven to form anywhere from 2 to 8 protuberances or hooks 136. Upon inserting the device 10 in an aperture in the left atrial appendage of the heart, the hooks 136 grip the outer portion of the left atrium heart tissue and thereby assist in keeping the device 130 from extruding out of the left atrial appendage with contraction of the heart. The proximal disc 134 is typically flat and similar to the disc formed by the proximal discs 18 in FIGS. 2-7. The proximal disc 134 abuts the inner atrial wall of the heart. Typically, the waist 20 will be about 4-8 mm in diameter. The length of the waist may range from 4 to 16 mm.

Figure 15:
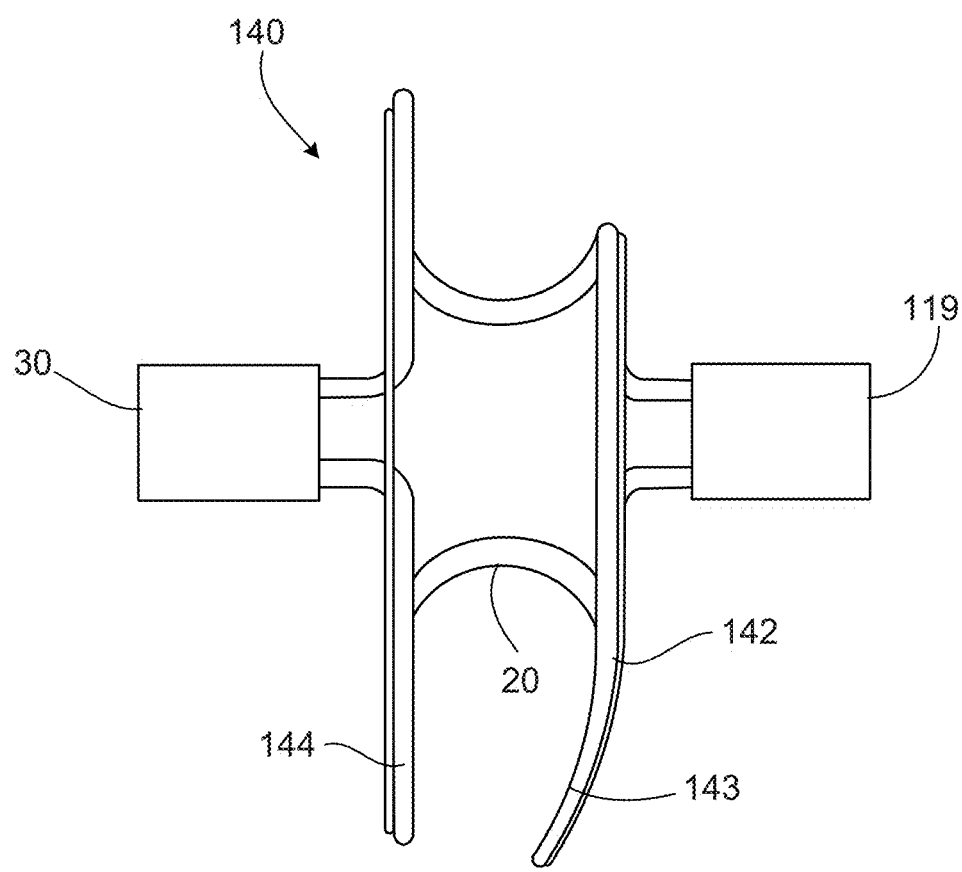
FIG. 15 is a side plan view of a fourth alternative embodiment of the occluder device of the present invention.

Reference is made to FIG. 15 for a fourth alternative embodiment of the occluder device 140. Occluder device 140 is intended to occlude perimembranous ventricular septal ("PVS") defects. This embodiment, like the embodiment shown in FIGS. 12A and 12B, uses four wires 112, 114, 116, 118 and two hubs 30, 119. The occluder device 140 is different from some embodiments in that two of the four wires form truncated distal-quarter discs, with the effect that the distal disc 142 substantially misses half of the disc. Therefore, the device 140 has approximately 1.5 discs as opposed to two discs. The half distal disc 142 is also significantly longer than the proximal disc 144. Typically, the distal disc 142 will be 6-8 mm in diameter. In addition, the distal disc 142 converges or curves inwards at 143, i.e., it is angled to contact the ventricular septum when the device 140 is inserted in the PVS defect. (See below for details.) The lower edge of the proximal disc (opposite to the long distal disc) will be 3-4 mm larger than the waist, and the other half of the proximal disc will be 2-3 mm larger than the waist. The discs can also be modified to be of different shapes in the same device. Alternatively, the disc angle may be created by a straight distal disc 142 angled with respect to the plane perpendicular to the waist 20 in a slant fashion.

Figure 16:
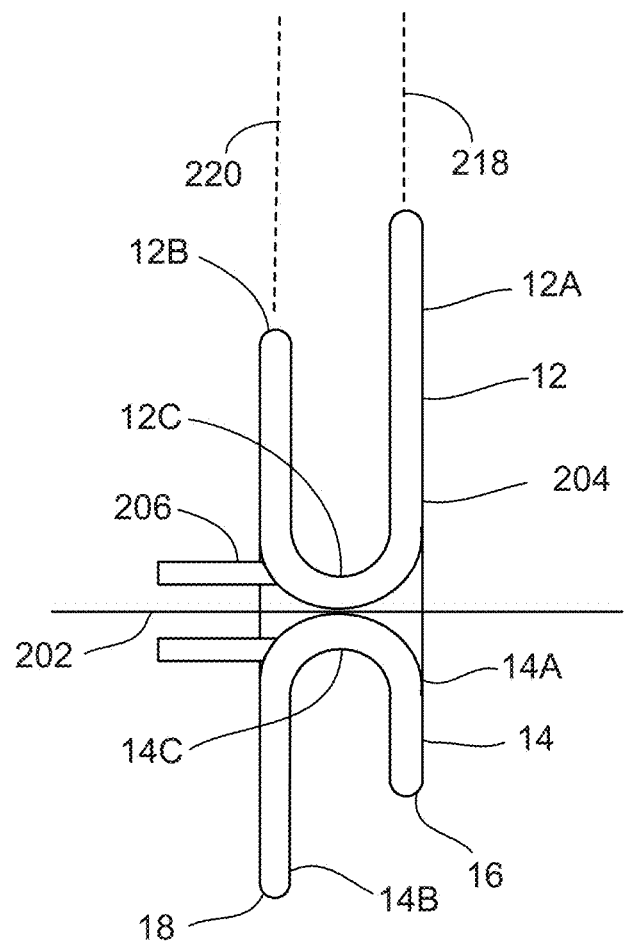
FIG. 16 is a side view of another exemplary alternative embodiment of the occluder device.

With reference to FIGS. 16-22, various additional exemplary alternative embodiments are provided with respect to the occluder device and/or components thereof With reference to FIG. 16, certain embodiments of the occluder device 10 may have one or more plates 16, 18 and/or geometric forms 12A, 12B, 14A, 14B of different sizes and/or configurations as compared with the embodiment described above in connection with FIG. 2. For example, the distal (or first) plate 16 and the proximal (or second) plate 18 may be offset with respect to the hub 30, and/or one side of a plate 16, 18 may be relatively higher or farther from the hub 30 than the other, for example via an oblique shift. In the particular embodiment of FIG. 16, a center 202 of the hub 30 is not aligned with (and, rather, is offset against) a center 204 of the first plate 16, but is aligned with a center 206 of the second plate 18. In another embodiment, the distal plate 16 and the proximal plate 18 are of equal size, yet off set from each other via a shift in opposite directions from the hub.

In certain embodiments, the first and second plates 16, 18 are configured such that a first segment formed from a first portion of the first wire 12 (for example, corresponding to form 12B of FIG. 16) has a first length, a second segment formed from a first portion of the second wire 14 (for example, corresponding to form 14A of FIG. 16) has a second length, a third segment formed for a second portion of the first wire 12 (for example, corresponding to form 12A of FIG. 16) has a third length, and a fourth segment formed for a second portion of the second wire 14 (for example, corresponding to form 14B of FIG. 16) has a fourth length. The second length is substantially equal to the first length. The third length is greater than the first length. The fourth length is substantially equal to the third length.

The semi-circle or half-disc 12A of the first wire 12 (also referenced above as the first geometric form 12A of the first wire 12) may differ in size (for example, having a larger radius and therefore a larger surface area) from the semi-circle or half-disc 14A of the second wire 14 (also referenced above as the first geometric form 14A of the second wire 14). In certain other embodiments, the semi-circle or half-disc 12A of the first wire 12 and the semi-circle or half-disc 14A of the second wire 14 may be of the same size same as one another, but may collectively form a distal plate 16 that differs in size from the proximal plate 18. In one such embodiment, the distal plate 16 is smaller in surface area than the proximal plate 18.

For example, the distal plate 16 may be of the same size as in FIG. 2, while the proximal plate 18 is larger in surface area than depicted in FIG. 2. This may occur, by way of example, when certain of the proximal quarter-circles of the second geometric forms 12B, 14B are larger in surface area than depicted in FIG. 2. Certain proximal quarter-circles of the second geometric forms 12B, 14B may be larger in surface area than other, adjacent quarter-circles of the second geometric forms 12B, 14B. Such differing sizes of the proximal quarter-circles of the second geometric forms 12B, 14B may be present regardless of the relative sizes of the distal and proximal plates 16, 18.

Figure 17:
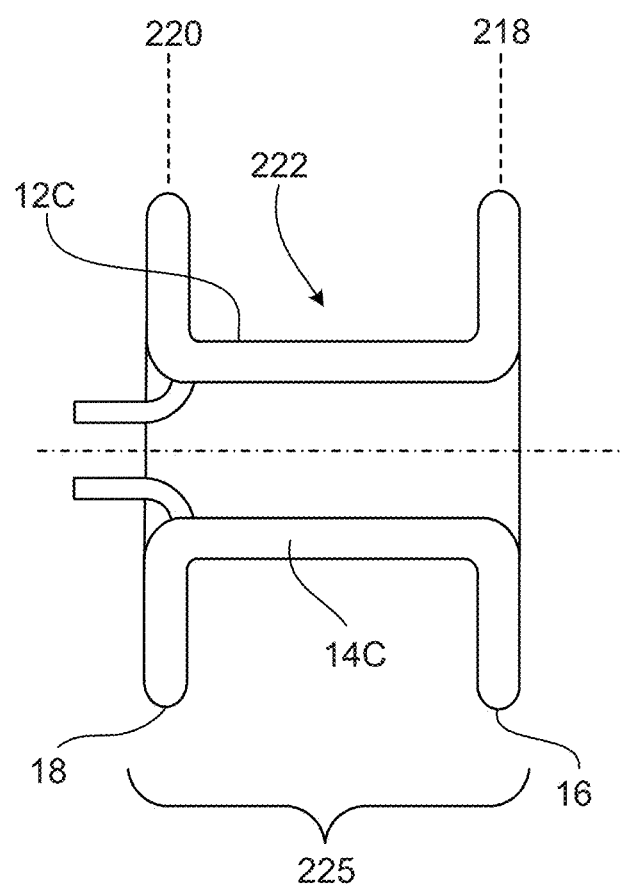
FIG. 17 is a side view of another exemplary alternative embodiment of the occluder device.

FIG. 17 depicts an embodiment of an occluder device contemplated herein with a wider waist 20. In one exemplary embodiment, the first plate 16 and the second plate 18 are disposed further apart as compared with the example of FIG. 2, so that a total length 225 of the waist 20 is greater than eight millimeters. Preferably, in this embodiment, the length 225 of the waist 20 is greater than eight millimeters and less than or equal to ten millimeters. In one such example, a straight-line distance between the first plane 218 and the second plane 220 of FIG. 2 is greater than eight millimeters, and is preferably also less than or equal to ten millimeters.

Figure 18:
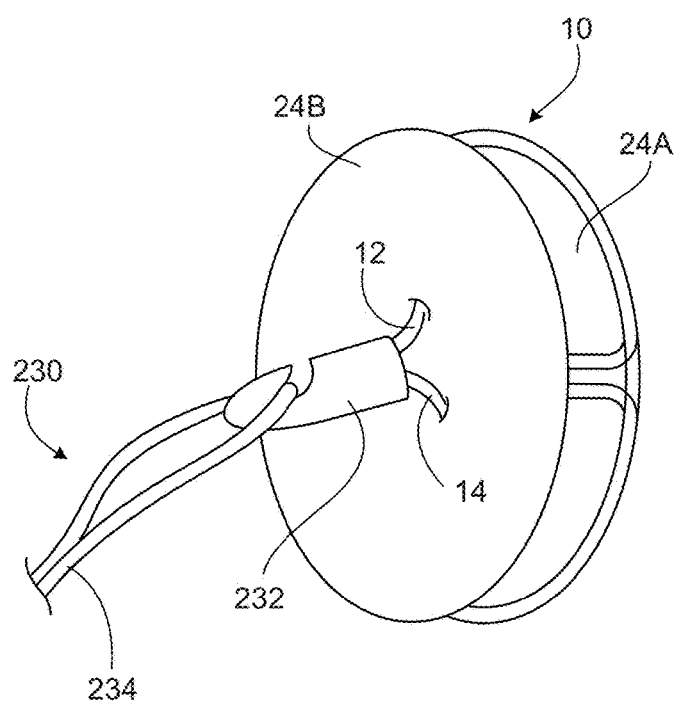
FIG. 18 is a perspective view of another exemplary alternative embodiment of the occluder device.

FIG. 18 depicts an embodiment of an occluder device contemplated herein with a hook engagement system 230. The hook engagement system 230 comprises a hook 232 and a lanyard 234 coupled thereto. The hook 232 is connected to the first plate 16 or the second plate 18 (and to the first and/or second wires 12, 14 thereof) described above, preferably proximate one of the coverings 24A, 24B. The hook engagement system 230 is configured for engagement with a positioning system (not depicted). In one embodiment, the hook engagement system 230 is used to remove the occluder device 10 from the heart. In this regard, a loop of the lanyard 234 is positioned onto the hook 232, and the lanyard 234 is pulled in the direction away from the heart, thus pulling the occluder device 10 through the heart aperture and through the body. In another embodiment, the positioning system comprises a deployment system for deploying the occluder device 10, for example by grasping the hook 232 for movement of the occluder device 10 into a human heart in a desired position proximate an aperture. In a further embodiment, the positioning system comprises a repositioning system for repositioning the occluder device 10, for example by grasping the hook 232 for adjusting the position of the occluder device 10 for more ideal placement of the occluder device 10 proximate an aperture. In certain embodiments, the lanyard (and/or another connection feature) is part of the positioning system, and the hook may exist separately from the occluder device 10. The hook 232 is preferably used in connection with a screw device for further engagement with the positioning system, such as a screw and nut system used in conjunction with FIGS. 8-10 described above. For example, the hook 232 may be positioned internal to a screw and nut system during placement of the device. Alternatively, the hook 232 may be used in connection with a thread cord through an eyelet or an opening, so that the cord would need to be pulled in order to lose the connection with the occluder device 10. In addition, such a cord may be used for retrieval of the occluder device 10, for example by including multiple lumens, preferably with an opening or slit, as part of a catheter delivery system. Other engagement and positioning systems are also contemplated, e.g., detent pin/receptacle, clasp/ball, clasp/eyelet, and the like.

Figure 19:
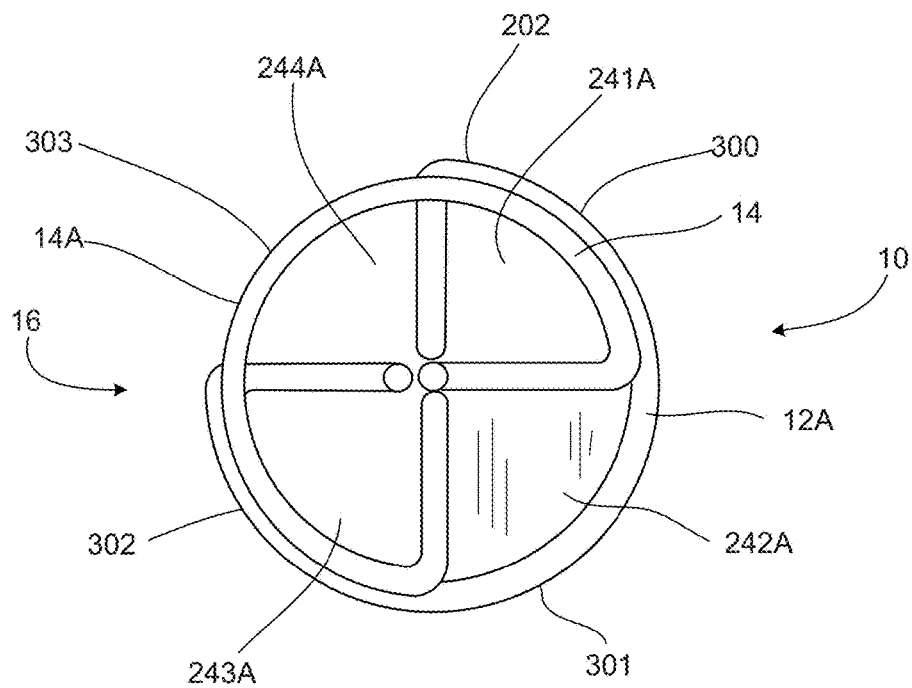
FIG. 19 is a plan view of another exemplary alternative embodiment of the occluder device, depicted with reference to planar quadrants in FIG. 19A.
Figure 19A:
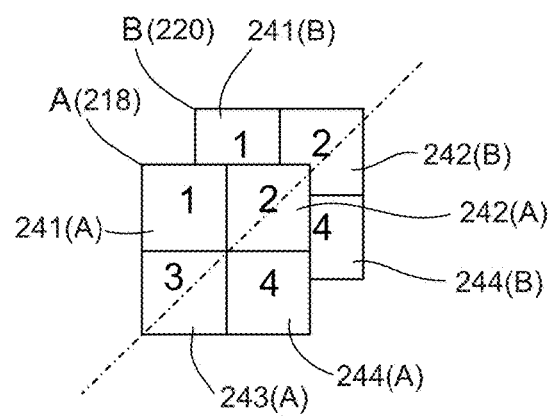

With reference to FIGS. 19 and 19A, an embodiment of an occluder device contemplated herein is depicted with overlapping wires at least at one plate. Overlapping wires add additional strength and rigidity to the plate of the occluder device. Specifically, the first geometric form 12A of the first wire 12 overlaps at least a portion of one region (for example, at least a portion of a common spatial quadrant, half-plane, and/or quartile) in common with the first geometric form 14A of the second wire 14 within the first plate 16. Alternatively, or in addition, the second geometric form 12B (not shown) of the first wire 12 overlaps at least a portion of one region (for example, at least a portion of a common spatial quadrant, half-plane, and/or quartile) in common with the second geometric form 14B (not shown) of the second wire 14 within the second plate 18 (not shown).

In a preferred embodiment, as illustrated in FIG. 19, the first geometric form 12A of the first wire 12 occupies at least three spatial quadrants 300, 301, and 302, two of which (namely, spatial quadrants 300 and 302) are shared in their entireties with the first geometric form 14A of the second wire 14. Likewise, the first geometric form 14A of the second wire 14 occupies at least three spatial quadrants 302, 303, and 300, two of which (namely, spatial quadrants 300 and 302) are shared in their entireties with the first geometric form 12A of the first wire 12. Similarly, the second geometric form 12B of the first wire 12 (not depicted in FIG. 19) occupies at least three spatial quadrants, two of which are shared in their entireties with the second geometric form 14B of the second wire 14 (not depicted in FIG. 19). Likewise, the second geometric form 14B of the second wire 14 occupies at least three spatial quadrants, two of which are shared in their entireties with the second geometric form 12B of the first wire 12.

FIG. 19A depicts an exemplary classification of planar quadrants for the first and second planes 218, 220 of FIG. 2 for reference with respect to the embodiment of FIG. 19. One skilled in the art will recognize that less or more than four quadrants can be utilized. With reference to FIG. 19A, the first plane 218 of FIG. 2 has a first quadrant 241(A), a second quadrant 242(A) that is adjacent to the first quadrant 241(A), a third quadrant 243(A) that is below the first quadrant 241(A), and a fourth quadrant 244(A) that is below the second quadrant 242(A) and adjacent to the third quadrant 243(A). The second plane 220 of FIG. 2 has a first quadrant 241(B), a second quadrant 242(B) that is adjacent to the first quadrant 241(B), a third quadrant 243(B) that is below the first quadrant 241(B), and a fourth quadrant 244(B) that is below the second quadrant 242 (B) and adjacent to the third quadrant 243(B). The first quadrant 241(A) of the first plane 218 is closer to the first quadrant 241(B) of the second plane 220 than to the second, third, or fourth quadrants 242(B), 243(B), 244(B) of the second plane 220. The second quadrant 242(A) of the first plane 218 is closer to the second quadrant 242(B) of the second plane 220 than to the first, third, or fourth quadrants 241(B), 243(B), 244(B) of the second plane 220. The third quadrant 243(A) of the first plane 218 is closer to the third quadrant 243(B) of the second plane 220 than to the first, second, or fourth quadrants 241(B), 242(B), 244(B) of the second plane 220. The fourth quadrant 244(A) of the first plane 218 is closer to the fourth quadrant 244(B) of the second plane 220 than to the first, second, or third quadrants 241(B), 242(B), 243(B) of the second plane 220.

With reference to the spatial quadrants set forth in FIG. 19A, in one preferred embodiment of FIG. 19, the first geometric form 12A of the first wire 12 extends through the first, second, and third quadrants 241(A), 242(A), 243(A) of the first plane 218. The first geometric form 14A of the second wire 14 extends through the first, third, and fourth quadrants 241(A), 243(A), and 244(A) of the first plane 218. Accordingly, in this embodiment, the first geometric forms 12A, 14A of the first and second wires 12, 14 share the first and third quadrants 241(A), 243(A) of the first plane 218 in common, for example to provide increased support and/or rigidity for the occluder device 10.

Also in one version of this embodiment of FIG. 19, the second geometric form 12B of the first wire 12 extends through the first, second, and third quadrants 241(B), 242(B), 243(B) of the second plane 220. The second geometric form 14B of the second wire 14 extends through the first, third, and fourth quadrants 241(B), 243(B), 244(B) of the second plane 220. Accordingly, in this version, the second geometric forms 12A, 14A of the first and second wires 12, 14 share the first and third quadrants 241(B), 243(B) of the second plane 220 in common, for example to provide increased support and/or rigidity for the occluder device 10.

However, this may vary in other versions or embodiments. For example, in another version of the embodiment depicted in FIG. 19, the second geometric form 12B of the first wire 12 extends through the third, fourth, and first quadrants 243(B), 244(B), 241(B) of the second plane 220, and the second geometric form 14B of the second wire 14 extends through the first, second, and third quadrants 241(B), 242(B), 243(B) of the second plane 220.

Figure 20:
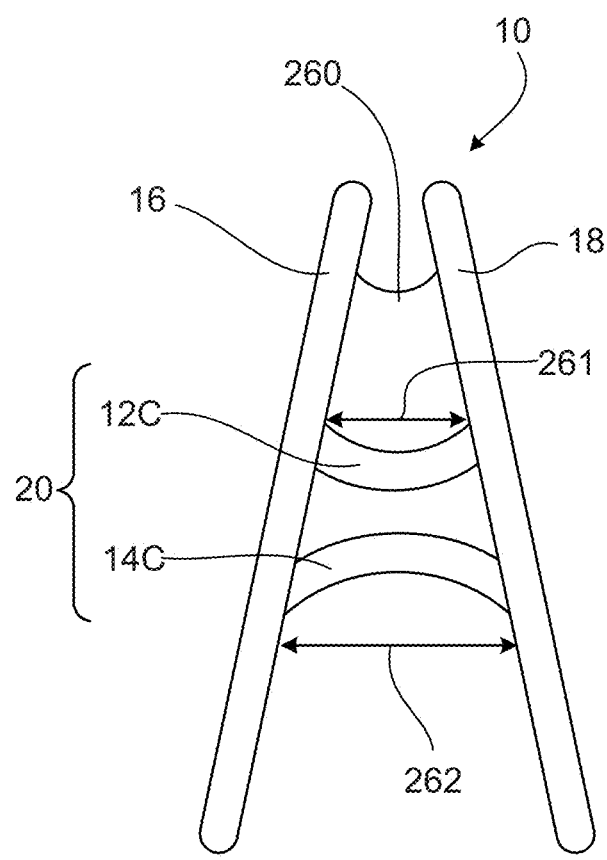
FIG. 20 is a side view of another exemplary alternative embodiment of the occluder device.
Figure 21A:
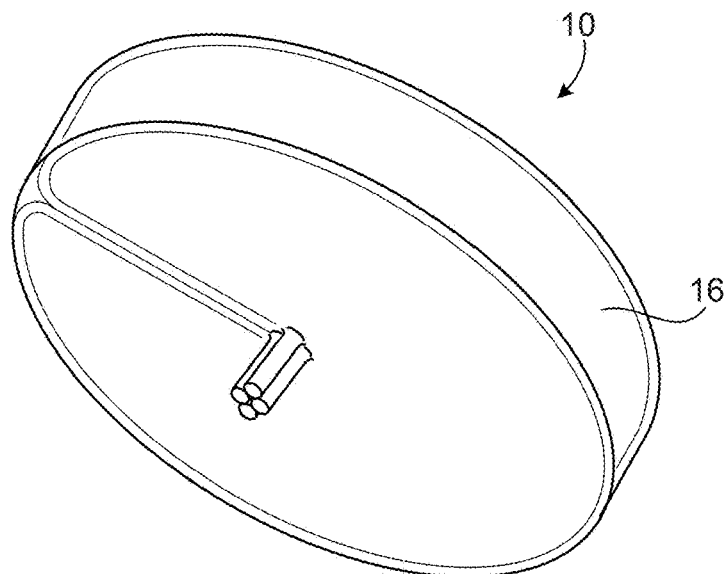
FIG. 21A is a perspective view of another exemplary alternative embodiment of the occluder device.
Figure 21B:
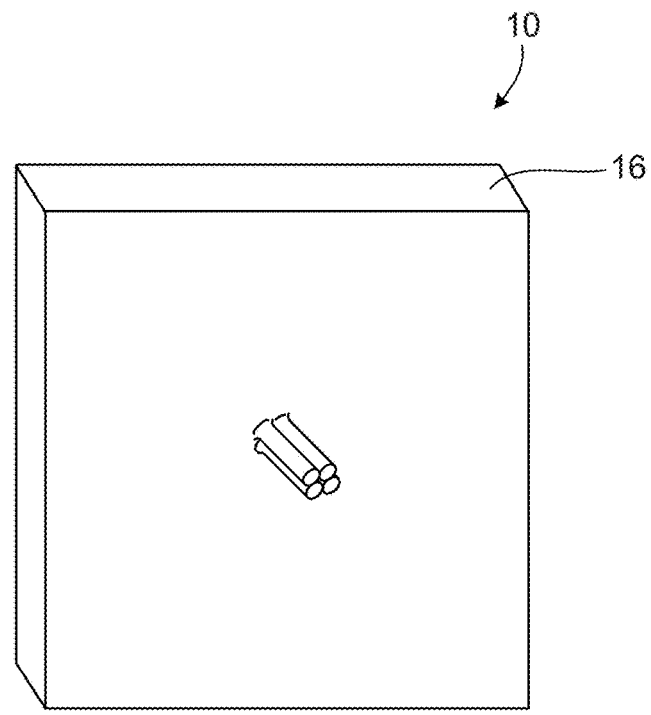
FIG. 21B is a plan view of another exemplary alternative embodiment of the occluder device.
Figure 21C:
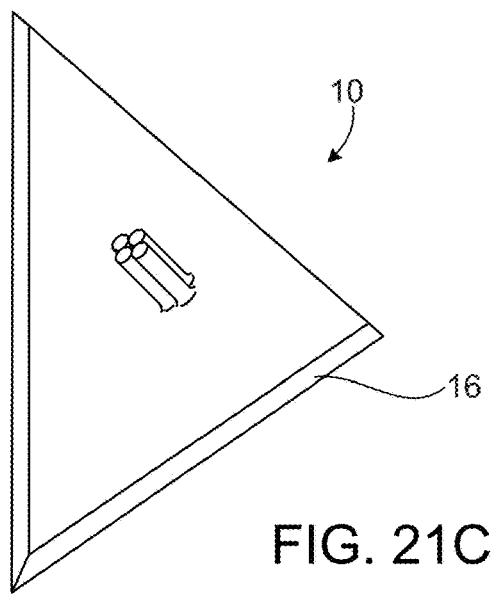
FIG. 21C is a plan view of another exemplary alternative embodiment of the occluder device.
Figure 21D:
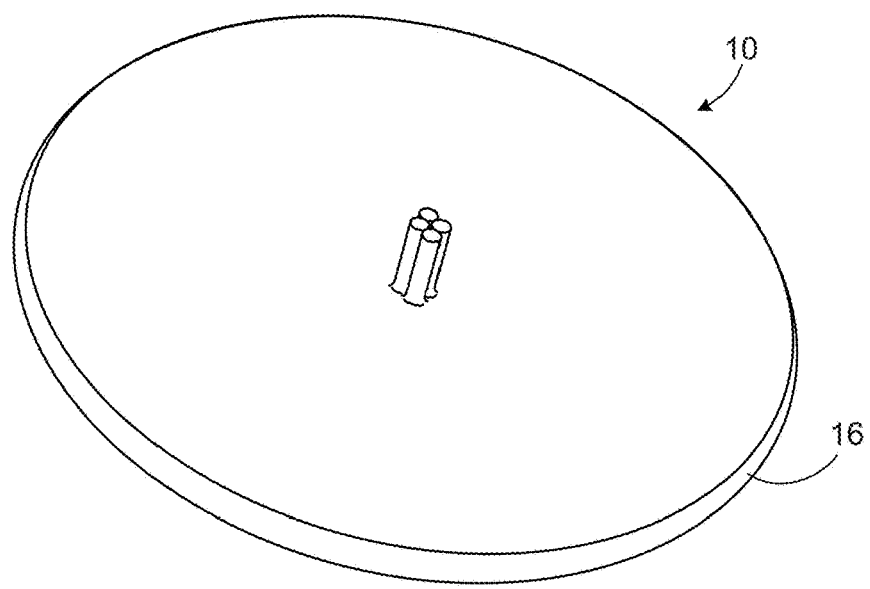
FIG. 21D is a plan view of another exemplary alternative embodiment of the occluder device.
Figure 21E:
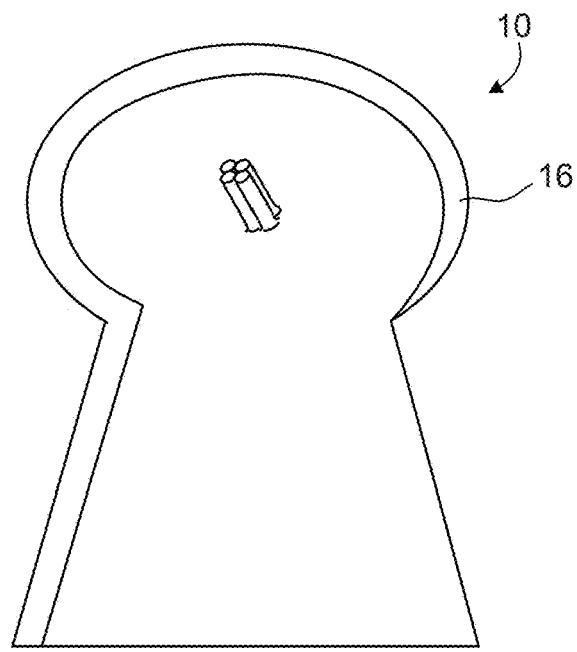
FIG. 21E is a plan view of another exemplary alternative embodiment of the occluder device.

FIG. 20 depicts an embodiment of an occluder device contemplated herein with a clothes-pin shape. In the embodiment of FIG. 20, the first plate 16 and the second plate 18 described above are non-parallel, and form a non-zero angle 260 with respect to one another. The angle 260 is preferably greater than five degrees, is more preferably greater than ten degrees, and is most preferably approximately equal to twenty degrees.

Also in the embodiment of FIG. 20, the waist 20 is configured such that the above-referenced waist components 12C of the first wire 12 and the waist components 14C of the second wire 14 are unequal in size. For example, as shown in FIG. 20, each waist component 12C of the first wire 12 has a first length indicated by double arrow 261, and each waist component 14C of the second wire 14 has a second length indicated by double arrow 262 that is greater than the first length. The length is defined as the distance between the first plate 16 and the second plate 18 taken from a predetermined distance from the occluder device 10's center point. Each waist component 14C of the second wire 14 may also have a greater surface area and radius as compared to respective waist components 12C of the first wire 12. In addition, in the embodiment of FIG. 20, the waist components 12C of the first wire 12 and the waist components 14C of the second wire 14 are preferably configured such that the waist 20 is curved, with a non-zero angle of curvature. The angle of curvature of the waist 20 is preferably greater than five degrees, is more preferably greater than ten degrees, and is most preferably greater than twenty degrees.

FIGS. 21A-21E depict an embodiment of an occluder device contemplated herein in which one or more of the first and second plates 16, 18 are non-circular in their geometric shape(s). In one embodiment of FIG. 21A, at least the first plate 16 has a generally oval shape. In an embodiment of FIG. 21B, at least the first plate 16 has a generally rectangular shape. In an embodiment of FIG. 21C, at least the first plate 16 has a generally triangular shape. In an embodiment of FIG. 21D, at least the first plate 16 has a generally elliptical shape. In an embodiment of FIG. 21E, at least the first plate 16 has a generally keyhole shape. In certain versions, the first plate 16 and/or the second plate 18 have generally the same geometric shapes as one another. In certain other versions, the first plate 16 and/or the second plate 18 differ from one another. The first plate 16 and the second plate 18 may also comprise any number of other different geometric shapes.

Figure 22:
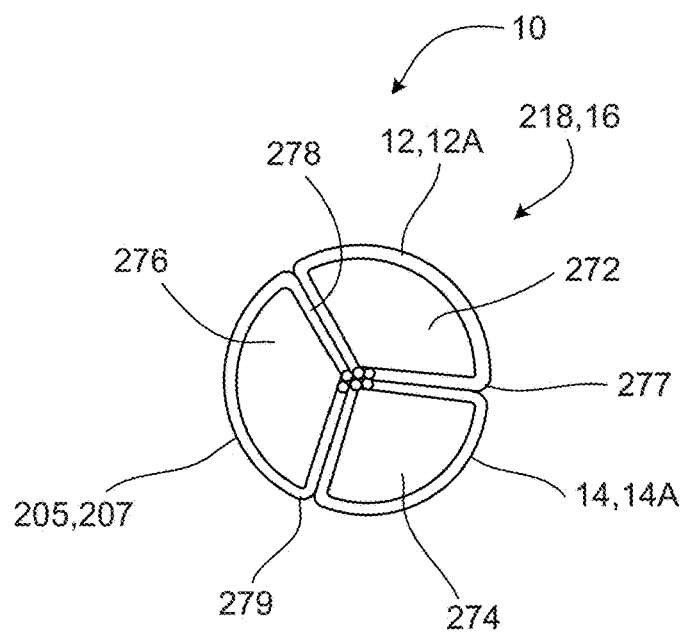
FIG. 22 is a plan view of another exemplary alternative embodiment of the occluder device.

FIG. 22 depicts an embodiment of an occluder device contemplated herein that is formed by more than two wires. Specifically, in the embodiment of FIG. 22, the occluder device 10 has three wires, namely: the first wire 12 and the second wire 14 described above, as well as a third wire 205. In some embodiments, four wires may be utilized. In some embodiments, six wires may be utilized. In some embodiments, the number of wires may differ further.

In the particular embodiment of FIG. 22, the three wires 12, 14, and 205 each form respective, non-overlapping thirds of each plane. Specifically, as depicted in FIG 22, the first geometric form 12A of the first wire 12 is disposed within and extends through a first region 272 of the first plane 218 described above. The second geometric form 12B of the second wire 14 is disposed within and extends through a second region 274 of the first plane 218. A first geometric form 207 of the third wire 205 is disposed within and extends through a third region 276 of the first plane 218. The first geometric forms 12A, 14A, 207 of the first, second, and third wires 12, 14, 205 collectively form the first plate 16.

Within the first plane 218, the first region 272 is adjacent to the second region 274, with a common border 277 formed by the first and second wires 12, 14. The first region 272 is also adjacent to the third region 276, with a common border 278 formed by the first and third wires 12, 205. In addition, the third region 276 is also adjacent to the second region 274, with a common border 279 formed by the second and third wires 14, 205.

Similarly, the second geometric form 12B of the first wire 12, the second geometric form 14B of the second wire 14, and a second geometric form of the third wire 205 would likewise be disposed within and extend through three similar adjacent, non-overlapping regions of the second plane 220, collectively forming the second plate 18 (not depicted in FIG. 22). The various first and second components of the first, second, and third wires 12, 14, and 205 are preferably curved with an arch, such as is shown in FIG. 22. Similar combinations of any number of different amounts of wires can similarly be used to form any number of different forms.

As mentioned above, in certain embodiments, the occluder device 10 may include multiple hubs 30, for example as depicted in FIG. 15. The number and configuration of such multiple hubs 30 may vary in different embodiments. In one such embodiment, a first end of the first wire 12 is disposed at a first hub 30, and at least one of the second end of the first wire 12, the first end of the second wire 14, and/or the second end of the second wire 14 is disposed at a second hub (such as hub 119 of FIGS. 12B, 13, and/or 15). In one such exemplary embodiment, the first and second ends of the first wire 12 are disposed at the first hub 30, and the first and second ends of the second wire 14 are disposed at the second hub (such as the second hub 119 of FIG. 15). In another such exemplary embodiment, the first ends of the first and second wires 12, 14 are disposed at the first hub 30, and the second ends of the first and second wires 12, 14 are disposed at the second hub (such as the hub 119 of FIGS. 12B, 13, and/or 15), among other possible variations.

Figure 23A:
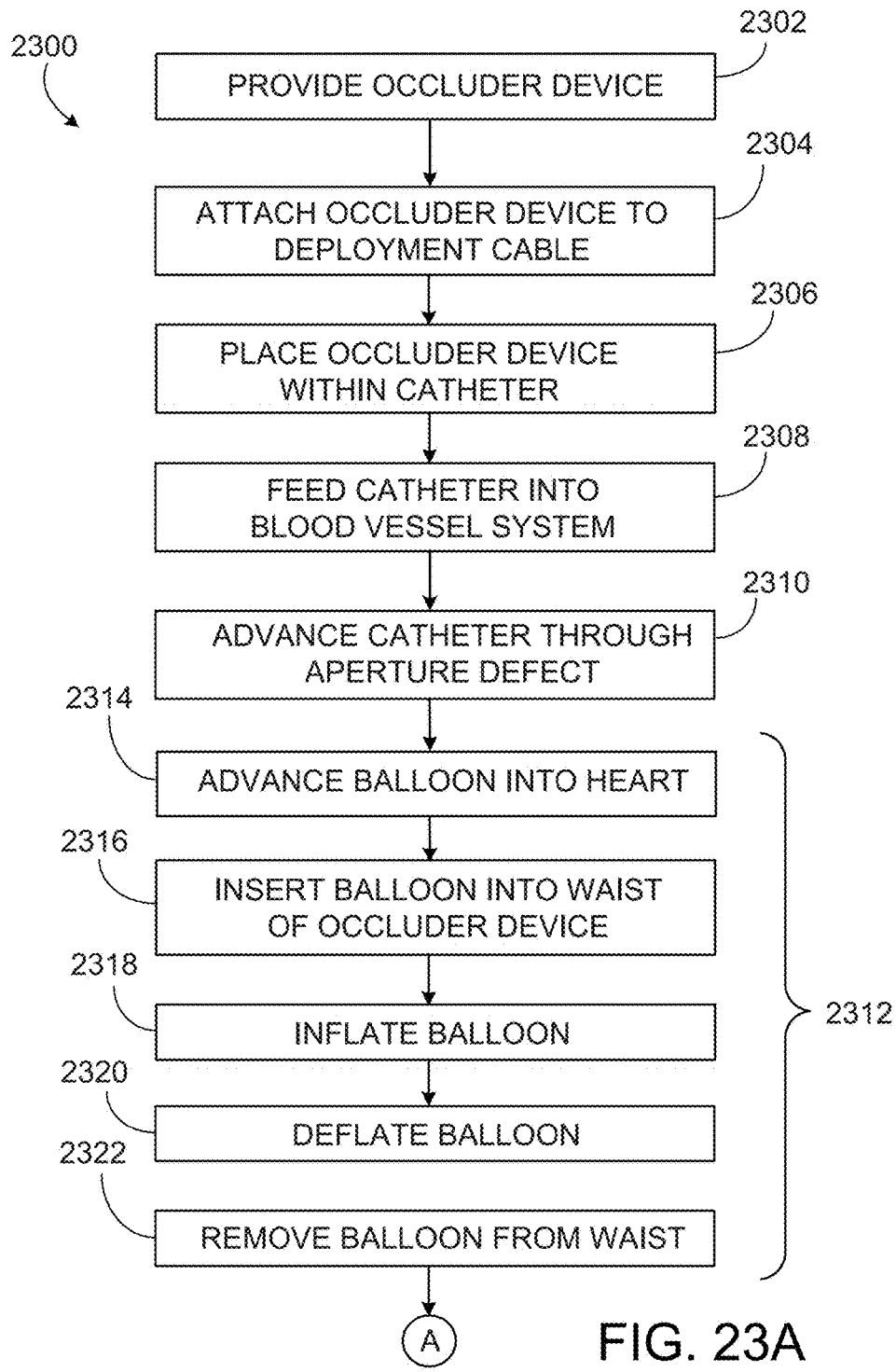
FIGS. 23A and 23B are a flowchart of an exemplary embodiment of a method for occluding an aperture defect in a heart to prevent the flow of blood therethrough, and that may be implemented using the occluder devices of FIGS. 2-22.
Figure 23B:
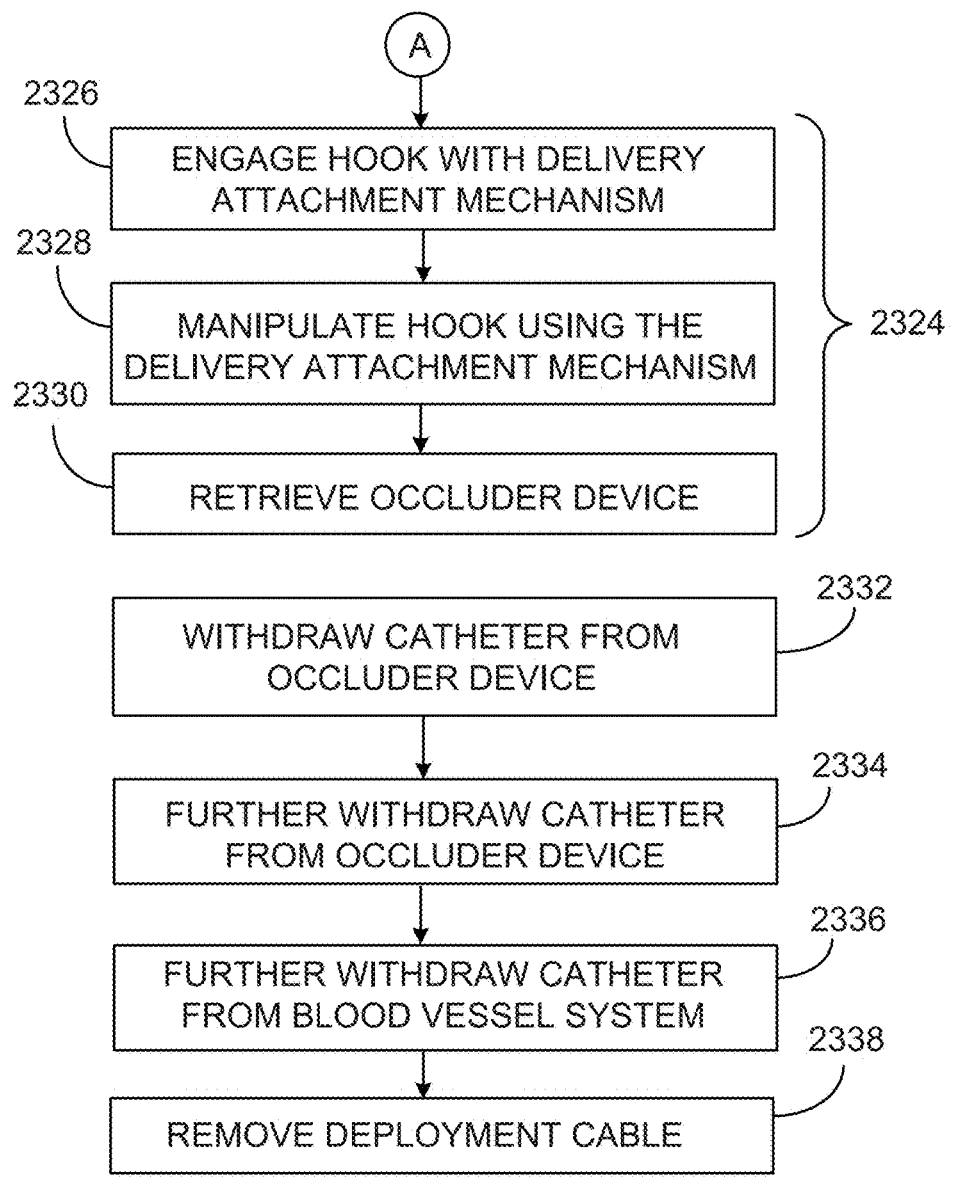

FIG. 23 is a flowchart of an exemplary embodiment of a method 2300 for occluding an aperture defect in a heart. The method 2300 can be utilized in connection with the heart 1 of FIG. 1 and the various embodiments of the occluder device 10 of FIGS. 2-22. Specifically, the method 2300 preferably utilizes one or more embodiments of the occluder devices 10 of FIGS. 2-22 to occlude an aperture defect of a heart, such as the aperture defect 6A of the heart 1 depicted in FIG. 1.

As depicted in FIG. 23, the method 2300 includes the step of providing an occluder device (step 2302). In various embodiments, the occluder device corresponds to the occluder device 10 depicted in any of the embodiments depicted in FIGS. 2-22 and/or described above. The occluder device preferably comprises a first flexible wire (such as wire 12 described above) and a second flexible wire (such as wire 14 described above). Each of the first and second wires is comprised of a shape memory material. Each of the first and second wires is shaped into first and second geometric forms (such as forms 12A, 12B, 14A, and 14B described above) around an inner region such that the first geometric form of the first wire and the first geometric form of the second wire form a first plate (such as plate 16 described above) in a first plane, and the second geometric form 12B of the first wire 12 and the second geometric form 14B of the second wire 14 form a second plate (such as plate 18 described above) in a second plane that is parallel to and remote from the first plane. The first and second plates are separated by a waist (such as waist 20 described above) formed from two portions of the first wire and two portions of the second wire. A sealed covering (such as covering 24A or 24B described above) is preferably disposed over at least one of the first and second plates. The covering provides a seal for the aperture defect (such as the defect 6A of the heart 1 described above). Each of the first and second wires has a first end and a second end. Each of the first and second ends of the first and second wires are connected to a hub (such as hub 30 described above). The hub further comprises a delivery attachment mechanism (for example, that includes or is used in connection with the catheter 40 described above) for attachment to a removable deployment cable (such as deployment cable 34 described above).

The method 2300 also includes the step of attaching the occluder device to the removable deployment cable (step 2304). The occluder device is placed within a flexible delivery catheter (such as the catheter 40 described above) having an open channel (such as the channel 42 described above) (step 2306). The catheter is fed into a blood vessel system (such as a blood vessel system of the heart 1 described above) and advanced via the blood vessel system to the aperture defect in the heart (step 2308). The catheter, with the occluder device disposed within, is similarly advanced through the aperture defect (step 2310).

In certain optional embodiments, a balloon sub-process 2312 is also utilized in occluding the aperture defect in the heart. In one such embodiment, depicted in FIG. 23, a balloon is advanced into the heart through the open channel toward the occluder device at the aperture defect (step 2314). The balloon is also inserted into the waist of the occluder device (step 2316). The balloon is then inflated (step 2318), in order to help position the occluder device proximate the heart defect. Once the occluder device is properly positioned, the balloon is deflated (step 2320) and then removed from the waist of the occluder device (step 2322).

In other optional embodiments, a hook sub-process 2324 may be utilized in occluding the aperture defect in the heart. In one such embodiment, depicted in FIG. 23, a hook (such as one or more of the hooks 136, 232 described above), is engaged with the delivery attachment mechanism (such as the catheter) (step 2326), preferably via a screw system. The hook is manipulated using the delivery attachment mechanism and used to reposition the occluder device (step 2328). In certain embodiments, the hook may also be utilized to retrieve the occluder device by exerting force on the delivery attachment mechanism in a direction away from the heart (step 2330).

The catheter next is withdrawn from the occluder device (step 2332). Preferably, the catheter is withdrawn from the occluder device in step 2332 in a manner such that the first plate of the occluder device expands on a first side of the aperture defect. In addition, the catheter is further withdrawn from the occluder device such that the second plate of the occluder device expands on a second side of the aperture defect (step 2334). Preferably, the catheter is withdrawn from the occluder device in step 2334 in a manner, such that the waist of the occluder device expands by memory retention within the aperture defect to self-center the occluder device. The catheter is then withdrawn from the blood vessel system (step 2336), and the deployment cable is removed from the hub of the occluder device (step 2338).

It will be appreciated that certain steps of the method 2300 may vary in certain embodiments. It will also be appreciated that certain steps of the method 2300 may occur in a different order than is depicted in FIG. 23. For example, the optional hook sub-process 2324 may be used before the optional balloon sub-process 2312. It will similarly be appreciated that certain steps of the method 230 may occur simultaneously with one another.

Figure 24A:
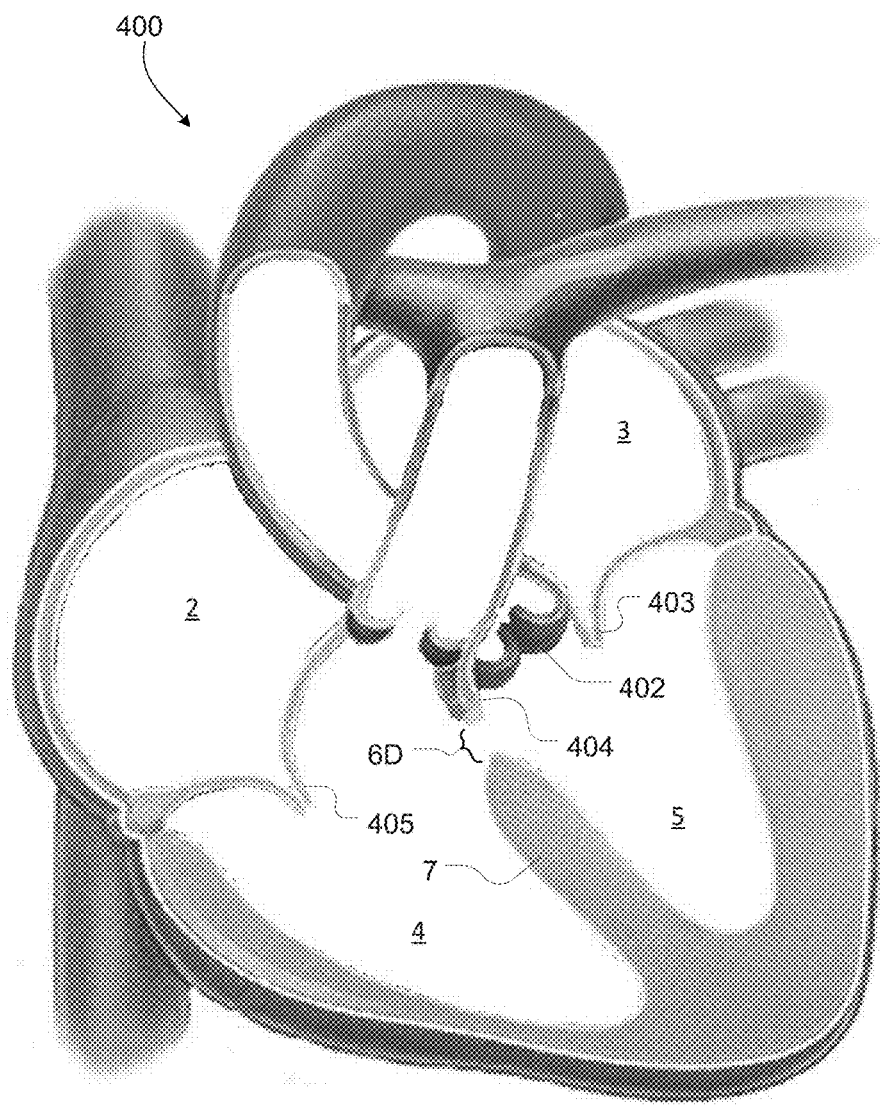
FIG. 24A is a schematic representation of a human heart including a perimembranous ventricular septal defect.

FIG. 24A is a schematic representation of a human heart 400 with a perimembranous VSD 6D. The heart 400 includes a right atrium 2, a left atrium 3, a right ventricle 4, and a left ventricle 5. The right ventricle 4 is separated from the left ventricle 5 by a ventricular septum 7. The ventricular septum 7 includes a perimembranous VSD 6D. The margins of the perimembranous VSD 6D are located partly in the membranous area of the ventricular septum 7 and partly in the muscular area of the ventricular septum 7. As depicted in FIG. 1, a perimembranous VSD 6D is located in an area of the ventricular septum 7 that is superior to a muscular VSD 6C.

A perimembranous VSD 6D can be more challenging to treat using an occlusion device than other types of VSDs, e.g., the muscular VSD 6C. One issue that makes perimembranous VSDs 6D more challenging to treat is their close proximity to other anatomical areas of the heart, such as the aortic valve 402, mitral valve 403, and tricuspid valve 405. In some instances, perimembranous VSDs 6D may be located juxta-aortic valve, juxta-mitral valve, and/or juxta-tricuspid valve. When treating perimembranous VSDs 6D using an occlusion device, any or all such valves can be potentially injured or impeded. For example, perimembranous VSDs 6D are often located in the left ventricle outflow tract just beneath the aortic valve 402. The short portion of the ventricular septum located superior to the perimembranous VSD 6D and inferior to the aortic valve 402 is the subaortic rim 404. Because of the close proximity to the aortic valve 402, the subaortic rim 404 area is generally too small to allow for a full occluder disc to be used in the left ventricle 5. That is, if a portion of an occluder disc is positioned on or applies pressure to the subaortic rim 404, the pressure or physical interference from the disc may impede the proper functioning of the aortic valve 402. Such pressure or physical interferences can result in adverse effects including, for example, aortic regurgitation.

Perimembranous VSDs 6D are also challenging to treat with an occlusion device because of their close proximity to the electrical conduction system of the heart known as the atrioventricular (AV) bundle. The AV bundle controls the contraction or beating of the chambers of the heart. The AV bundle includes specialized muscle fibers that regulate the heartbeat by conducting impulses from the AV node in the right atrium 2 to the right and left ventricles 4 and 5. A portion of the AV bundle tends to be located at the superior margin of a perimembranous VSD 6D, that is, in the subaortic rim 404 area. If pressure is applied to the subaortic rim 404 containing the AV bundle, the AV electrical signal can be slowed or disrupted, and cardiac arrhythmia can result. If an occluder device for treating a perimembranous VSD 6D contacts the subaortic rim 404, the pressure exerted on the AV bundle can result in adverse effects such as cardiac arrhythmia.

Accordingly, to avoid such adverse effects, in some embodiments it may not be practical or desirable to use a full 360 degree circular disc (a "full disc") on the left side of an occlusion device, i.e., in the left ventricle 5. Rather, in some embodiments, a portion of a full disc (a "partial disc") can be advantageously used on the left side. For example, in some embodiments, a partial disc having an arc of 180-240 degrees may be desirable. In some embodiments, a partial disc comprising a semi-circle of approximately 180 degrees is used on the left side. In some embodiments, a partial disc comprising a circular sector with an arc of less than 180 degrees is used. The partial disc can be oriented in relation to the heart 400 to substantially avoid contact with or applying pressure onto the subaortic rim 404. In some embodiments, the partial disc comprises two or more portions, or sub-discs, as described further below in reference to FIG. 26-28.

Figure 24B:
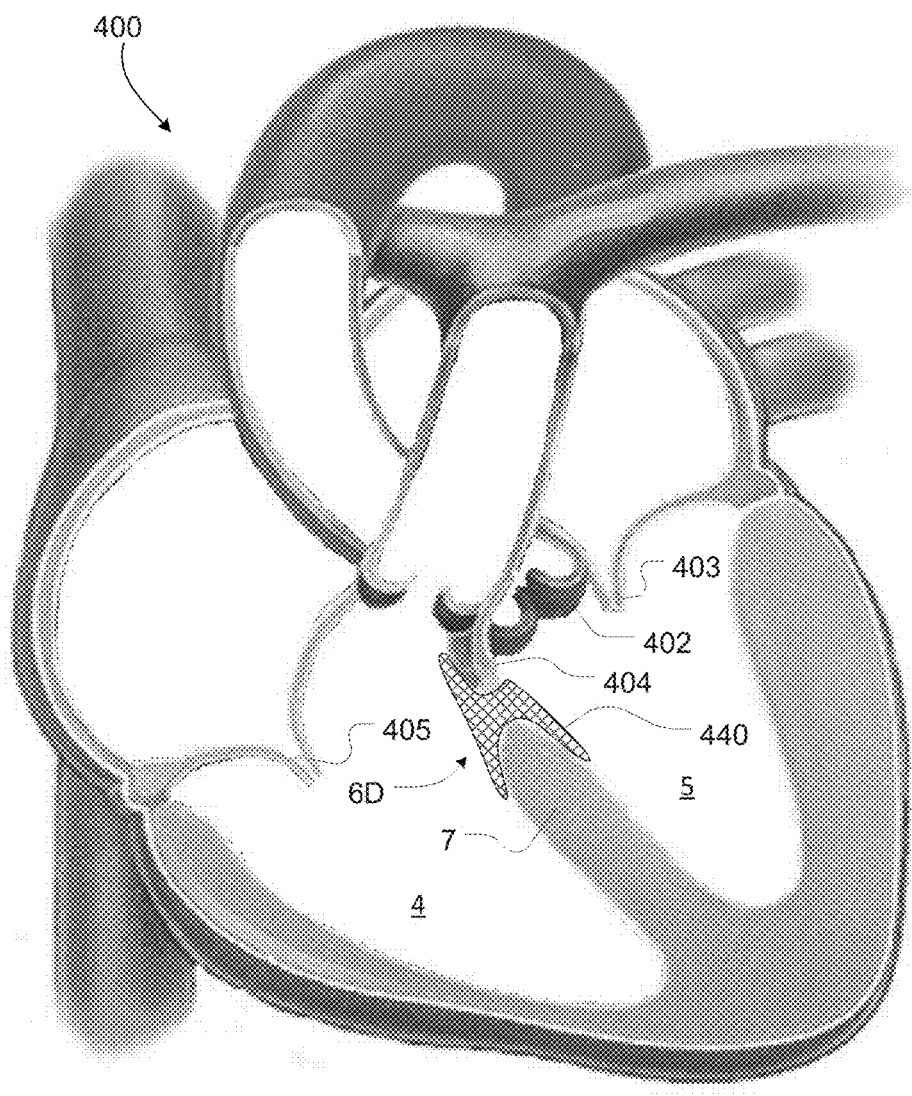
FIG. 24B is the schematic representation of the human heart of FIG. 24A including an exemplary asymmetrical occlusion device.

FIG. 24B is a schematic representation of a human heart 400, and a schematic representation of an asymmetrical occlusion device 440 installed in the perimembranous VSD 6D of the heart 400. In some embodiments, the asymmetrical occlusion device 440 is well-suited for treating a perimembranous VSD 6D because the asymmetrical occlusion device 440 does not make substantial contact with the subaortic rim 404. In some embodiments, the asymmetrical occlusion device 440 (shown in a side view) includes a full disc on the right side, i.e. in the right ventricle 4. On the left side, i.e., in the left ventricle 5, the asymmetrical occlusion device 440 includes a partial disc. In some embodiments, the partial disc contacts portions of the ventricular septum 7 that are located inferior to the subaortic rim 404 while avoiding substantial contact with the subaortic rim 404 or with the aortic valve 402, mitral valve 403, and tricuspid valve 405. An asymmetrical occlusion device 440 having such a partial disc configuration on the left side can occlude a perimembranous VSD 6D while avoiding adverse interference with one or more of the aortic valve 402, mitral valve 403, tricuspid valve 405, and/or the AV bundle of the heart 400.

Figure 25:
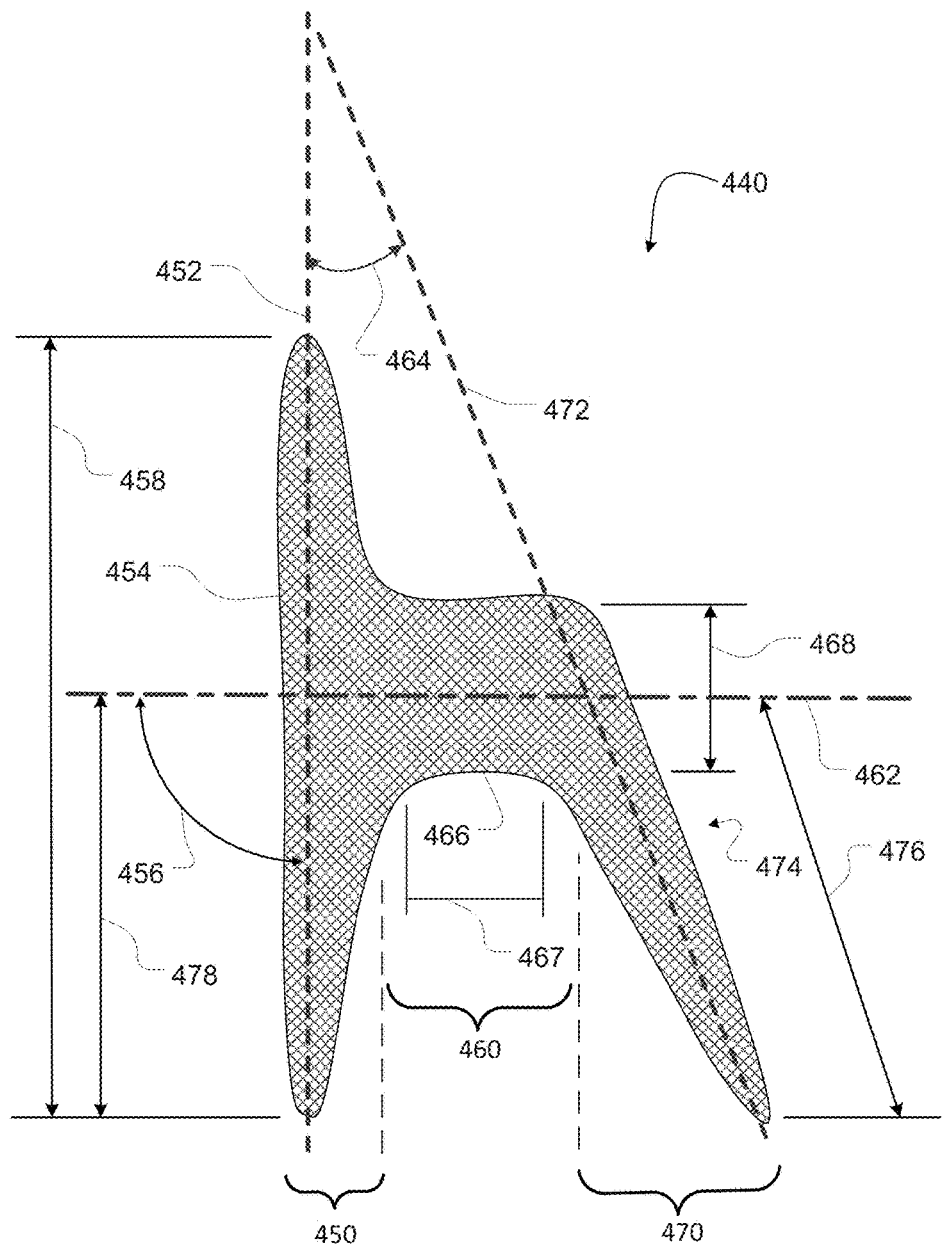
FIG. 25 is a schematic side view representation of an exemplary embodiment of an asymmetrical occlusion device.

FIG. 25 is a side view of a schematic illustration of the example asymmetrical occlusion device 440. In general, the asymmetrical occlusion device 440 includes three regions: (i) an occluder region 450, (ii) an attachment region 460, and (iii) a securing region 470. The attachment region 460 can interconnect the occluder region 450 to the securing region 470.

In some embodiments, the occluder region 450 includes a full disc 454 (shown in side view). When the asymmetrical occlusion device 440 is implanted in a heart to treat a perimembranous VSD, the full disc 454 can be located in the right ventricle abutting the ventricular septum (also refer to FIG. 24B). The full disc 454 may also be referred to as the proximal disc, because the full disc 454 can be proximal to a delivery catheter whereas the rest of the asymmetrical device 440 can be distal to the delivery catheter. The full disc 454 has a diameter 458 and a radius 478. In some embodiments, the diameter 458 is in the range of about 20-26 mm, about 16-30 mm, or about 10-36 mm. The diameter 458 is typically selected in general accordance with the size of the heart and the size of the VSD being treated. The full disc 454 defines at least one disc plane 452. Because FIG. 25 shows a side view of the asymmetrical occlusion device 440, the disc plane 452 is along the line shown for disc plane 452 and 90 degrees to the surface of the figure.

In some embodiments, the attachment region 460 of the asymmetrical occlusion device 440 includes a waist 466. When the asymmetrical occlusion device 440 is implanted in a heart, the waist 466 can pass through the aperture of the perimembranous VSD. In some embodiments, the waist 466 defines a transverse cross-sectional shape that can be represented by a circle with a diameter 468. In some embodiments, the waist diameter 468 is in the range of about 12-18 mm, about 8-22 mm, or about 4-26 mm. The waist diameter 468 can be selected in correlation with the size of the aperture of the perimembranous VSD being treated. In some patients, the aperture of the perimembranous VSD will be substantially non-circular, such as elliptical. In cases when the aperture is elliptical, in some embodiments the waist diameter 468 is selected in correlation to the minor axis of the elliptical aperture. In some embodiments, the waist 466 has an axial length 467. The axial length 467 can be selected in correlation to the axial length of the tunnel of the perimembranous VSD being treated. In some embodiments, the axial length 467 of the occluder device is adjustable by the clinician in situ during the implantation procedure. The attachment region 460 can define a longitudinal axis 462.

In some embodiments, the securing region 470 includes a partial disc 474. When the asymmetrical occlusion device 440 is implanted in a heart to treat a perimembranous VSD, the partial disc 474 can be located on the ventricular septum in the left ventricle such that the partial disc 474 is generally inferior to the aperture of the perimembranous VSD. The partial disc 474 may also be referred to as the distal disc because, during implantation of the asymmetrical device 440, the partial disc 474 can be distal in relation to the delivery catheter, whereas the rest of the asymmetrical device 440 can be proximal to the delivery catheter. As described further below in reference to FIG. 26, in some embodiments the partial disc 474 includes multiple portions or securing members (e.g., 480, 482, and 484 of FIG. 26) each having a major axis. In some embodiments, the major axes of the securing members generally define a partial disc plane 472. In some embodiments, the major axes of the securing members may not all reside on a common plane (see e.g., FIG. 28). The partial disc 474 can have a length 476 that generally defines, for example, the length of the securing members as measured from axis 462 to the free-ends of the securing members. In some embodiments, the length 476 is approximately equal to the radius 478 of the full disc 454. However, in some embodiments, the length 476 of the partial disc 474 is less than or greater than the radius 478 of the full disc 454. In some embodiments, the partial disc 474 has multiple securing members with disparate lengths (see e.g., FIG. 27A).

The relative orientations of the occluder region 450, attachment region 460, and securing region 470 with respect to each other will now be described. While the asymmetrical occlusion device 440 shown in FIG. 25 is used to explain the configuration of the regions with respect to each other, the example asymmetrical occlusion device 440 is merely one example embodiment of the occlusion devices provided herein. Other embodiments having regional configurations that are different than asymmetrical occlusion device 440 are also envisioned within the scope of this disclosure.

The angular relationship between the disc plane 452 and the axis 462 of the attachment region 460 is represented by angle 456. In the example asymmetrical occlusion device 440 embodiment shown, the axis 462 of the attachment region 460 is generally perpendicular to disc plane 452. That is, in this example, angle 456 is approximately 90 degrees. In some embodiments, the angle 456 is more than or less than 90 degrees (see e.g., FIG. 28). In general, the selection of an asymmetrical occlusion device 440 with a particular angle 456 can be made in accordance with the anatomy of the patient. That is, in some patients the aperture of the perimembranous VSD will be generally orthogonal to the nearby surface of the ventricular septum in the right ventricle. In that case, an asymmetrical occlusion device 440 with an angle 456 of about 90 degrees would be appropriate to treat the VSD. In some patients, the aperture of the perimembranous VSD may be at a non-orthogonal angle in relation to the nearby surface of the ventricular septum in the right ventricle. In such cases, an asymmetrical occlusion device 440 with an angle 456 that approximately matches the non-orthogonal angle of the aperture in relation to the nearby surface of the ventricular septum can be selected. In some embodiments, the angle 456 of the occluder device is adjustable by the clinician either before the implantation procedure or in situ during the implantation procedure.

The angular relationship between the disc plane 452 and the partial disc plane 472 is represented by angle 464. In the example asymmetrical occlusion device 440, the angle 464 is approximately 20 degrees. However, in some embodiments, the angle 464 is zero degrees. That is, in some embodiments the disc plane 452 and the partial disc plane 472 are substantially parallel to each other. In some embodiments, the angle 464 is within a range of about 0-60 degrees, about 10-50 degrees, or about 20-40 degrees. The angle 464 can be selected in accordance with the anatomy of the patient. Some patients may have the left and right surfaces of the ventricular septum near the perimembranous VSD substantially parallel to each other. In that case, an asymmetrical occlusion device 440 with an angle 464 of zero degrees may be selected. However, in some patients the left and right surfaces of the ventricular septum near the perimembranous VSD may be at a non-zero angle in relation to each other. In such cases, an asymmetrical occlusion device 440 with an angle 464 that is approximately equal to the angle between the left and right surfaces of the ventricular septum near the perimembranous VSD may be selected. In some embodiments, the angle 464 of the occluder device is adjustable by the clinician either before the implantation procedure or in situ during the implantation procedure.

It should be recognized that in some embodiments the force exerted on the ventricular septum by the full disc 454 and the partial disc 474 should be only a light pressure. A light amount of pressure can help the asymmetrical occlusion device 440 maintain proper position in relation to the anatomy of the patient's heart. However, too much pressure from the asymmetrical occlusion device 440 may induce adverse effects, such as adverse effects to the heart valves and AV bundle as described above.

Figure 26:
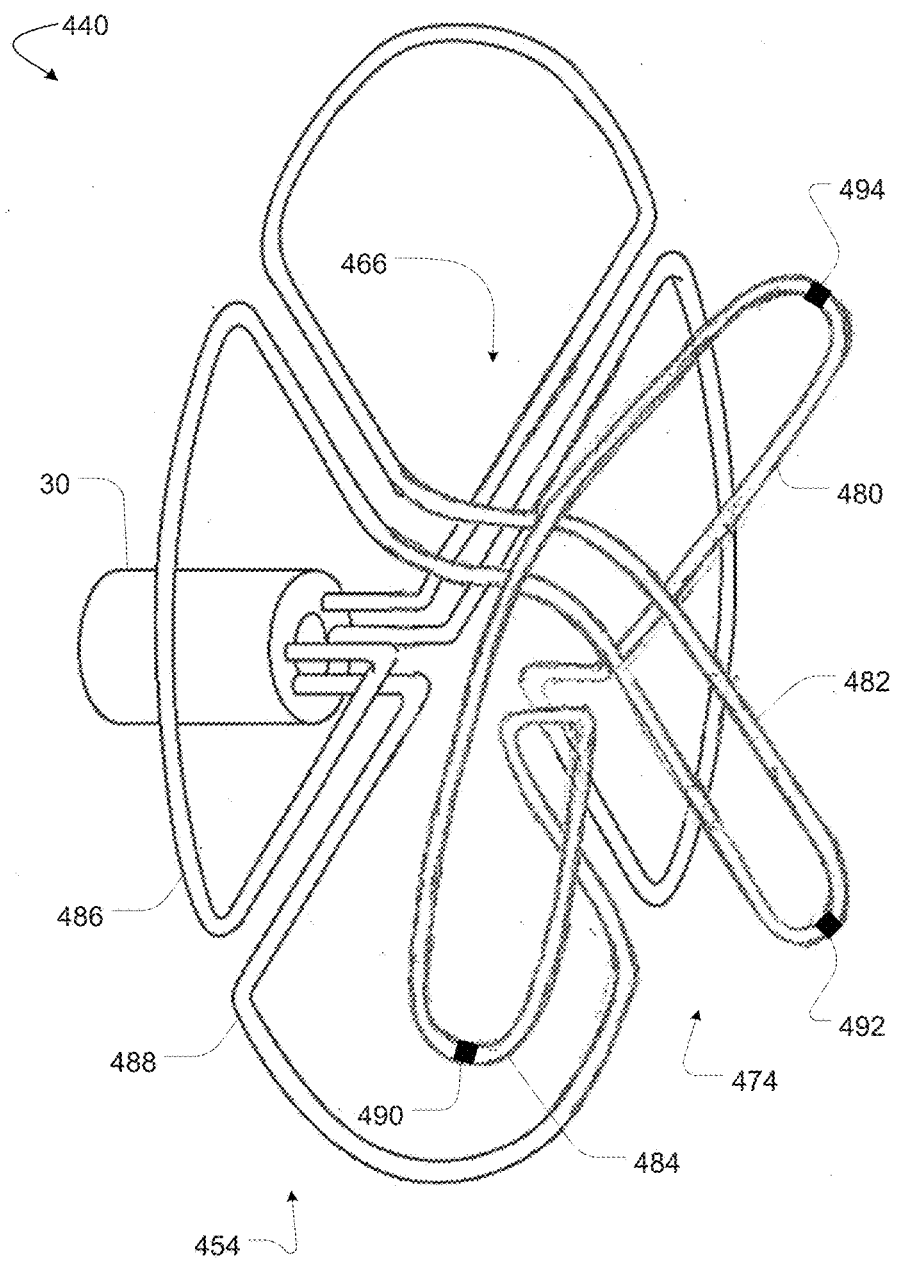
FIG. 26 is a perspective view of an exemplary embodiment of an asymmetrical occlusion device.

FIG. 26 is a perspective view of an example asymmetrical occlusion device 440. In general, the asymmetrical occlusion device 440 includes a full disc 454, a waist 466, a partial disc 474, and a delivery attachment hub 30. The asymmetrical occlusion device 440 embodiment comprises two separate uniquely shaped memory wires 486 and 488. The wires 486 and 488 can be substantially similar to the wires 12 and 14 described above. While the example asymmetrical occlusion device 440 includes two wires 486 and 488, some embodiments use one wire, three wires, or four wires or more to form an asymmetrical occlusion device.

In some embodiments, the asymmetrical occlusion device 440 is self-centering. In some embodiments, the waist 466 is made of four wire portions as shown. In some embodiments, the waist 466 is made of more or fewer than four wire portions. In some embodiments, the wire portions of waist 466 substantially conform to the size and shape of the aperture of a perimembranous VSD. In some embodiments, the wire portions of waist 466 exert enough radial force to provide a self-centering feature, while not pressing against the aperture edges in a manner that exacerbates the defect or affects the functioning of the heart valves or AV bundle.

In some embodiments, the wire portions of the waist 466 are more rigid than the wire portions of the full disc 454 and the partial disc 474. In other words, in some embodiments, physical conformance by the asymmetrical occlusion device 440 to the landscape of the ventricular septum is primarily as a result of deflection by the full disc 454 and/or partial disc 474 rather than by deflection of the wire portions of the waist 466. In some such embodiments, the waist 466 should not inhibit the abilities of the full disc 454 and the partial disc 474 to conform to the topography of the underlying tissue that the discs 454 and 474 make contact with. In some embodiments, the asymmetrical occlusion device 440 is fully repositionable and retrievable after deployment.

In some embodiments, the full disc 454 and the partial disc 474 have membranous coverings similar to those of other embodiments described above (see e.g., FIGS. 6 and 7). In some embodiments, neither the full disc 454 nor the partial disc 474 have membranous coverings. In some embodiments, either the full disc 454 or the partial disc 474 has a membranous covering, while the other does not have a membranous covering. In some embodiments, the membranous coverings can ensure more complete coverage and occlusion of the aperture, and promote encapsulation and endothelialization of tissue to encourage anatomical closure of the aperture. The membranous coverings can be substantially as described above in reference to coverings 24A and 24B. In some embodiments, the encapsulation and endothelialization of tissue promoted by the membranous coverings avoid a need for supplementary anchoring devices, such as barbs and hooks. In some embodiments, supplementary anchoring devices are included irrespective of the presence of membranous coverings.

The partial disc 474 of example asymmetrical occlusion device 440 includes three securing members 480, 482, and 484. In some embodiments, each securing member 480, 482, and 484 is individually flexible. As such, the securing members 480, 482, and 484 are individually conformable to the topography of the ventricular septum tissue with which the securing members 480, 482, and 484 make contact. This configuration can help prevent or minimize device trauma to the ventricular septum, while substantially securing the asymmetrical occlusion device 440 in the desired location on the ventricular septum. Adverse effects, such as aortic regurgitation and cardiac block, can thereby be minimized or avoided altogether—despite the close proximity of the perimembranous VSD to the heart valves and AV bundle.

In some embodiments, the three securing members 480, 482, and 484 each include one or more visualization markers, such as radiopaque markers 490, 492, and 494. The markers can assist a clinician with radiographic visualization of the asymmetrical occlusion device 440 so that the clinician can orient the device as desired in relation to the anatomy of the patient. Radiopaque markers can also be included on other locations on the asymmetrical occlusion devices. In some embodiments, materials are added to the frame elements to enhance visualization of the frame elements.

The transcatheter implantation procedure of an asymmetrical occlusion device can be performed substantially as described in reference to FIGS. 8-10 above. In some embodiments, restriction wires are included to restrict the circumference of the waist 466, as desired.

Figure 27A:
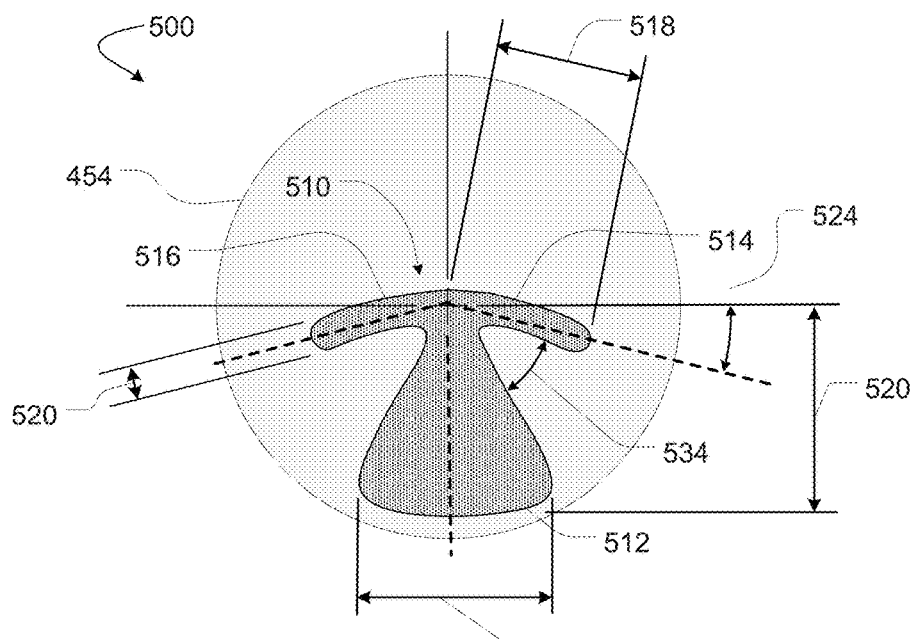
FIGS. 27A and 27B are schematic representations of two exemplary embodiments of asymmetrical occlusion devices.
Figure 27B:
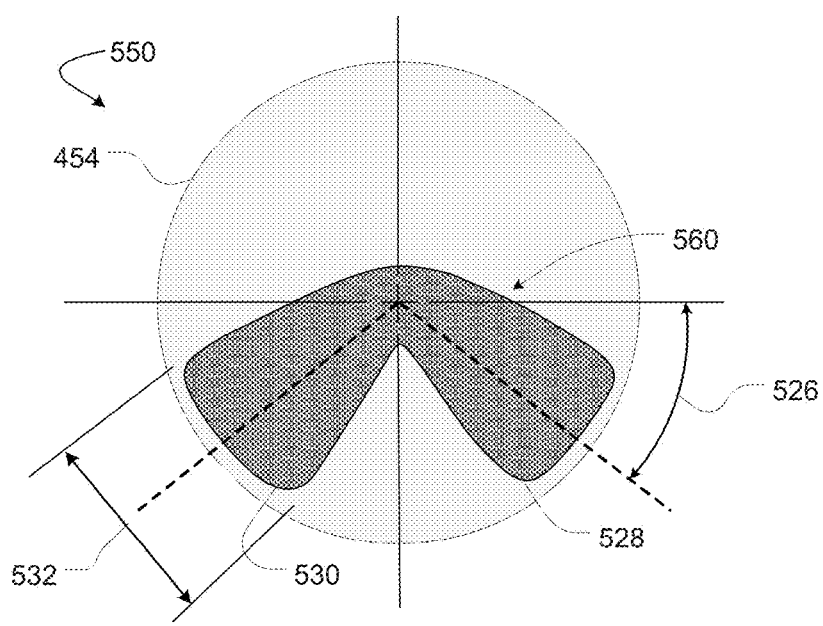

FIGS. 27A and 27B are schematic representations of two embodiments of asymmetrical occlusion devices 500 and 550. These example embodiments illustrate some of the different design configurations that are possible by adjusting various features of the asymmetrical occlusion devices provided herein. For example, by altering certain features of the partial disc as described below, multiple design configurations and combinations are possible.

FIG. 27A illustrates an asymmetrical occlusion device 500 having a full disc 454 and a partial disc 510. The partial disc 510 includes three securing members 512, 514, and 516. In this embodiment, the side securing members 514 and 516 are mirror images of each other. In some embodiments, each securing member has its own unique design. In some embodiments, the partial disc 510 can be asymmetrical such that none of the securing members mirror each other.

The lengths and widths of the various securing members 512, 514, and 516 can be determined to provide the particular desired features of the partial disc 510. For example, in the embodiment of partial disc 510, the length 518 of the securing members 514 and 516 is less than the length 520 of the securing member 512. In some embodiments, the lengths of the securing members are greater than the radius of the full disc 454. In some embodiments, such as asymmetrical occlusion device 500, the lengths of the securing members are less than the radius of the full disc 454. Additionally, the widths of the securing members can be individually distinct, or the widths can be equivalent to the widths of other securing members. For example, the width 520 of securing members 514 and 516 are equal to each other and less than the width 522 of the securing member 512. In some embodiments, each securing member has an individually unique length and/or width. In some embodiments, two or more of the securing members, (but not all) have their lengths or widths in common. In some embodiments, all securing members have their lengths and widths in common.

Additional partial disc design characteristics that can provide particular desired features can include, for example, the number of securing members and the angular positioning of the securing members. For example, as the asymmetrical occlusion device 500 shows, in some embodiments three securing members 512, 514, and 516 are used. In some embodiments, more or fewer than three securing members are used. For example, in some embodiments, a single securing member is used as the partial disc. In some embodiments, four or more securing members are used as the partial disc.

The angular positions of the securing members can also be established as desired. For example, angle 524 of asymmetrical occlusion device 500 represents the angular position of the securing members 514 and 516 in relation to a plane containing the axis 504. In some embodiments, the angle 524 is approximately zero. In some embodiments, the angle 524 is anywhere between 0-90 degrees. For example, the angular position of securing member 512 in relation to a plane containing the axis 504 is approximately 90 degrees. As depicted by asymmetrical occlusion device 550, in some embodiments the angle 526 is approximately 45 degrees. As discussed above in reference to FIG. 25, the relative angles of the planes 452, 472 defined by the full disc 454 and the partial disc 474 are another design characteristic that can be selected in some embodiments.

In some embodiments, an open space 534 is located between adjacent securing members. In some embodiments, the securing members abut one another such that there is substantially no space between the edges of adjacent securing members. In some embodiments, the edges of adjacent securing members overlap each other.

In some embodiments, individual securing members are asymmetrical. That is, rather than having shapes that are mirror images of each other on opposite sides of its longitudinal axis, the shapes on opposite sides of the longitudinal axis can be different from each other. For example, in some embodiments, one side of a securing member has a substantially straight edge, while the other side of the same securing member has a curved edge.

FIG. 27B schematically depicts an asymmetrical occlusion device 550 including a full disc 454 and a partial disc 560. The partial disc 560 includes two securing members 528 and 530. In this embodiment, the two securing members 528 and 530 are mirror images of each other. However, in some embodiments, each securing member has its own unique design. In some embodiments, at least one securing member has a design unique from one or more of the other securing members. The securing members 528 and 530 are depicted as having an angular position of angle 526 in relation to the plane containing the axis 554. In this embodiment, the angle 526 is approximately 45 degrees. In some embodiments, angles of 0-90 degrees are possible.

Securing members 528 and 530 are depicted as having relatively wide widths 532 (as compared to securing members 514 and 516, for example). In some embodiments, such wide securing members may advantageously distribute the clamping forces exerted by the securing members over a larger area of the ventricular septum. By distributing the clamping force over a larger area, the pressure exerted on the ventricular septum can be lowered while maintaining a sufficient clamping force to substantially secure the occlusion device in the desired location.

Figure 28:
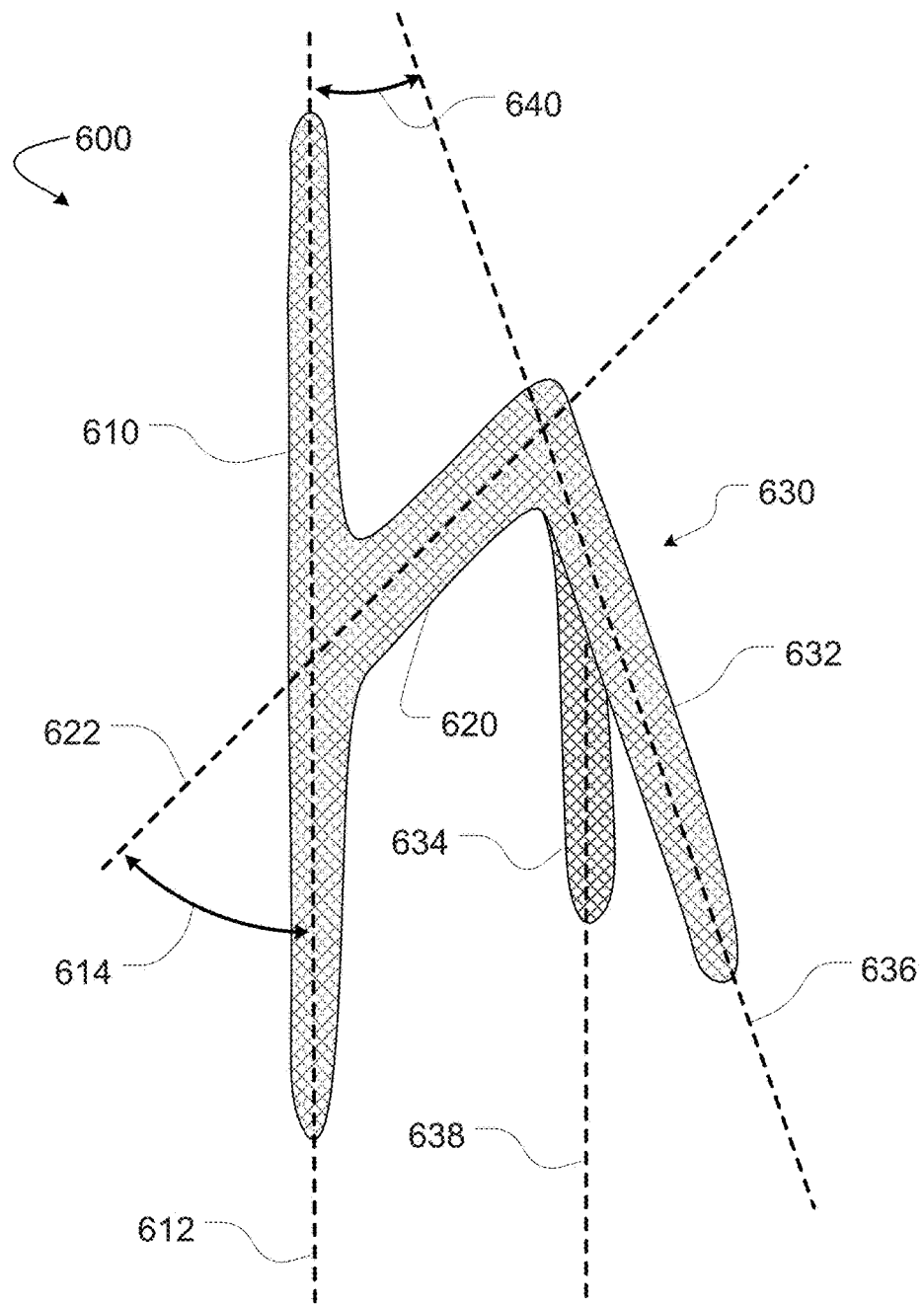
FIG. 28 is a schematic side view representation of another exemplary embodiment of an asymmetrical occlusion device.

FIG. 28 is a side view of a schematic representation of another embodiment of an asymmetrical occlusion device 600. This embodiment includes a full disc 610 with a disc plane 612, a waist 620 with an axis 622, and a partial disc 630 with securing members 632 and 634 having axes 636 and 638 respectively.

The asymmetrical occlusion device 600 illustrates additional design variations in regard to how the regions of an asymmetrical occlusion device can be configured in relation to each other. For example, the axis 622 of the waist 620 is at an acute angle 614 in relation to the disc plane 612. Such a feature can be useful, for example, with perimembranous VSD apertures that are at a non-orthogonal angle in relation to the nearby surface of the ventricular septum in the right ventricle. In addition, the asymmetrical occlusion device 600 illustrates that individual securing members can each be oriented at different angles in relation to the full disc plane 612. For example, the axis 636 of securing member 632 is at an acute angle 640 in relation to the disc plane 612, while the axis 638 of securing member 634 is approximately parallel to the disc plane 612. The ability to have securing members at various angles in relation to the full disc plane 612 can enable an asymmetrical occlusion device to be shaped in correlation to the particular anatomy of the patient, and result in less potential for disruption to the heart valves and AV bundle.

Some embodiments may comprise any combinations of the embodiments described herein and/or described in the drawings. It is understood that the disclosure is not confined to the particular construction and arrangement of parts herein illustrated and described, but embraces such modified forms thereof as come within the scope of the following claims. Additionally, it will be appreciated that various embodiments may be freely combined together, and/or that various features of different embodiments may be freely combined together.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

We claim:

1. A method for occluding a defect in an anatomical feature using an occluder device defining a proximal end and a distal end and including a plurality of wires each extending continuously between the proximal and distal ends of the device and forming a proximal disc defining a proximal outer perimeter of the device, a distal disc defining a distal outer perimeter of the device, and a waist arranged between the proximal disc and the distal disc and defining a narrowed region of the device between the proximal and distal outer perimeters, the method comprising:
    traversing a delivery catheter through the defect;
    deploying the distal disc by advancing the occluder device from the delivery catheter to expand the distal disc;
    deploying the waist section by further advancing the occluder device from the delivery catheter to expand the waist and positing the waist within the defect;
    deploying the proximal disc by advancing the occluder device from the delivery catheter to expand the proximal disc and fully deploying the occluder device such that each of the plurality of wires include: a first linear section extending radially outward from the central axis of the device toward the proximal outer perimeter of the device, a first curved transition extending between the first linear section and the proximal outer perimeter of the device, a second curved transition extending from the proximal outer perimeter of the device toward the central axis of the device, a central curved transition extending through the narrowed region of the device such that the narrowed region of the device is configured to extend through a defect in an anatomical feature, a third curved transition extending from the narrowed region of the device to the distal outer perimeter of the device, the central curved transition positioned between the second and third curved transitions, a fourth curved transition extending from the distal outer perimeter of the device toward the central axis of the device, and a second linear section extending radially inward from the fourth curved transition toward the central axis of the device; and
    releasing the occluder device from the delivery catheter.

2. The method of claim 1, wherein the deploying the distal disc includes expanding the distal disc to include a circular outer perimeter and deploying the proximal disc includes expanding the proximal disc to include a circular outer perimeter.

3. The method of claim 1, wherein fully deploying the occluder device includes conforming the occluder device to the defect.

4. The method of claim 1, wherein releasing the occluder device from the delivery catheter includes releasing a tether from the occluder device.

5. The method of claim 1, wherein the occluder device further comprises a covering arranged on the plurality of wires.

6. The method of claim 5, wherein the covering is configured to cover the distal disc, the proximal disc, and the waist.

7. The method of claim 1, further comprising repositioning the occluder device after releasing the occluder device from the delivery catheter.

8. The method of claim 7, wherein repositioning the occluder device comprises adjusting a position of the occluder device within the defect.

9. The method of claim 1, wherein the defect is an atrial septal defect ("ASD"), a patent foramen ovale ("PFO"), a ventricular septal defect ("VSD"), or a patent ductus arteriosus ("PDA").

10. A method for occluding a defect in an anatomical feature using an occluder device, the method comprising:
    arranging a distal disc of the occluder device on a distal side of the defect;
    arranging a waist section defining a narrowed region of the occluder device within the defect; and
    deploying the occluder device to a fully deployed configuration by arranging a proximal disc of the occluder device on a proximal side of the defect;
    wherein the occluder device comprises a plurality of wires having a first linear section extending radially outward from a central axis of the device toward a proximal outer perimeter of the device, a first curved transition extending between the first linear section and the proximal outer perimeter of the device, a second curved transition extending from the proximal outer perimeter of the device toward the central axis of the device, a central curved transition extending through the narrowed region of the device, a third curved transition extending from the narrowed region of the device to a distal outer perimeter of the device, the central curved transition positioned between the second and third curved transitions, a fourth curved transition extending from the distal outer perimeter of the device toward the central axis of the device, and a second linear section extending radially inward from the fourth curved transition toward the central axis of the device.

11. The method of claim 10, wherein the defect is an atrial septal defect ("ASD"), a patent foramen ovale ("PFO"), a ventricular septal defect ("VSD"), or a patent ductus arteriosus ("PDA").

12. The method of claim 11, wherein the occluder device further comprises a covering arranged on the plurality of wires to cover the distal disc, the proximal disc, and the waist.

13. The method of claim 12, wherein the deploying the occluder device to the fully deployed configuration comprises sealing the defect.

14. The method of claim 13, wherein sealing the defect includes the covering promoting tissue ingrowth.

15. The method of claim 10, wherein the deploying the occluder device to the fully deployed configuration comprising conforming the occluder device to the defect.

16. The method of claim 10, wherein the deploying the occluder device to the fully deployed configuration comprising self-expanding the occluder device.

17. The method of claim 16, wherein the plurality of wires comprise a shape memory material.

18. A method for occluding a defect in an anatomical feature using an occluder device having a plurality of wires extending from a proximal end to a distal end, the method comprising:
  delivering the occluder device to a location of the defect with the occluder device in an elongated configuration in which the occluder device includes a plurality of wires arranged within a delivery sheath, and
  transitioning the occluder device from the elongated configuration to a deployed configuration by extending the plurality of wires from the delivery sheath such that a distal disc of the occluder device is arranged on a distal side of the defect, a waist section defining a narrowed region of the occluder device is arranged within the defect, and a proximal disc of the occluder device is arranged on a proximal side of the defect, the deployed configuration including the plurality of wires forming a first linear section extending radially outward from a central axis of the device toward a proximal outer perimeter of the device, a first curved transition extending between the first linear section and the proximal outer perimeter of the device, a second curved transition extending from the proximal outer perimeter of the device toward the central axis of the device, a central curved transition extending through the narrowed region of the device, a third curved transition extending from the narrowed region of the device to a distal outer perimeter of the device, the central curved transition positioned between the second and third curved transitions, a fourth curved transition extending from the distal outer perimeter of the device toward the central axis of the device, and a second linear section extending radially inward from the fourth curved transition toward the central axis of the device.

19. The method of claim 18, wherein the occluder device further comprises a covering arranged on the plurality of wires to cover the distal disc, the proximal disc, and the waist.

20. The method of claim 18, wherein transitioning the occluder device from the elongated configuration to the deployed configuration comprises causing the occluder device to self-expand.

* * * * *